(12) United States Patent
Sanders

(10) Patent No.: US 10,524,954 B2
(45) Date of Patent: Jan. 7, 2020

(54) METHODS AND DEVICES FOR TREATING SLEEP APNEA AND SNORING

(75) Inventor: Ira Sanders, North Bergen, NJ (US)

(73) Assignee: Linguaflex, Inc., Davie, FL (US)

( * ) Notice: Subject to any disclaimer, the term of this patent is extended or adjusted under 35 U.S.C. 154(b) by 1436 days.

(21) Appl. No.: 11/672,019

(22) Filed: Feb. 6, 2007

(65) Prior Publication Data

US 2007/0261701 A1    Nov. 15, 2007

Related U.S. Application Data

(63) Continuation-in-part of application No. 10/597,590, filed as application No. PCT/US2005/006430 on Feb. 28, 2005, now Pat. No. 8,925,551.

(60) Provisional application No. 60/765,638, filed on Feb. 6, 2006, provisional application No. 60/547,897, filed on Feb. 26, 2004.

(51) Int. Cl.
  *A61F 5/56* (2006.01)
  *A61B 17/04* (2006.01)
  *A61F 2/00* (2006.01)
  *A61B 17/06* (2006.01)
  (Continued)

(52) U.S. Cl.
  CPC .......... *A61F 5/566* (2013.01); *A61B 17/0401* (2013.01); *A61F 2/00* (2013.01); *A61B 2017/0417* (2013.01); *A61B 2017/0419* (2013.01); *A61B 2017/0496* (2013.01); *A61B 2017/06052* (2013.01); *A61B 2017/248* (2013.01); *A61B 2017/306* (2013.01); *A61B 2017/308* (2013.01)

(58) Field of Classification Search
  CPC ........ A61F 5/56; A61F 5/566; A61F 2005/56; A61F 2017/248

USPC ................... 128/848, 846; 433/140
See application file for complete search history.

(56) References Cited

U.S. PATENT DOCUMENTS

| | | |
|---|---|---|
| 3,517,669 A | 6/1970 | Buono et al. |
| 3,659,612 A | 5/1972 | Shiley et al. |
| (Continued) | | |

FOREIGN PATENT DOCUMENTS

| | | |
|---|---|---|
| DE | 197 56 956 | 7/1999 |
| JP | 2000-060862 | 2/2000 |
| (Continued) | | |

OTHER PUBLICATIONS

International Search Report to PCT/US2009/60991, dated Jan. 7, 2010, 3 pages.

(Continued)

*Primary Examiner* — Victoria J Hicks
(74) *Attorney, Agent, or Firm* — The Webb Law Firm

(57) ABSTRACT

Embodiments of the invention include methods and devices to prevent or treat upper airway disorders in mammals related to impaired airflow. One aspect of this invention is a tongue retractor (LTR) that indirectly retracts tongue base by its implant site in the frenulum area. This simplifies the insertion, adjustment and maintenance of the device. Another aspect of this invention describes a highly localized and fully implantable LTR that is inserted into the base of tongue to stiffen lax surface mucosa or mechanically couple it to internal tongue structures. Another aspect of this invention is an LTR inserted in or around the pharyngoglossal fold. This site allows retraction and stiffening of tongue base tissue as well as the soft palate and lateral pharyngeal wall.

12 Claims, 23 Drawing Sheets

(51) Int. Cl.
  *A61B 17/24* (2006.01)
  *A61B 17/30* (2006.01)

(56) References Cited

U.S. PATENT DOCUMENTS

| | | | |
|---|---|---|---|
| 4,254,774 A | 3/1981 | Boretos | |
| 4,335,723 A | 6/1982 | Patel | |
| 4,387,879 A | 6/1983 | Tauschinski | |
| 4,704,111 A | 11/1987 | Moss | |
| 4,907,602 A | 3/1990 | Sanders | |
| 4,981,477 A | 1/1991 | Schon et al. | |
| 5,109,850 A | 5/1992 | Blanco et al. | |
| 5,190,053 A | 3/1993 | Meer | |
| 5,250,049 A | 10/1993 | Michael | |
| 5,364,410 A | 11/1994 | Failla et al. | |
| 5,376,110 A | 12/1994 | Tu et al. | |
| 5,443,477 A | 8/1995 | Marin et al. | |
| 5,464,395 A | 11/1995 | Faxon et al. | |
| 5,480,420 A | 1/1996 | Hoegneld et al. | |
| 5,498,247 A | 3/1996 | Brimhall | |
| 5,591,216 A | 1/1997 | Testerman et al. | |
| 5,694,922 A | 12/1997 | Palmer | |
| 5,792,067 A | 8/1998 | Karell | |
| 5,797,913 A | 8/1998 | Dambreville et al. | |
| 5,843,021 A | 12/1998 | Edwards et al. | |
| 5,954,050 A | 9/1999 | Christopher | |
| 5,961,440 A * | 10/1999 | Schweich, Jr. | A61B 17/00234 600/16 |
| 5,976,109 A | 11/1999 | Heruth | |
| 5,980,557 A | 11/1999 | Iserin et al. | |
| 5,988,171 A | 11/1999 | Sohn et al. | |
| 5,989,244 A | 11/1999 | Gregory et al. | |
| 5,997,567 A | 12/1999 | Cangelosi | |
| 6,013,728 A | 1/2000 | Chen et al. | |
| 6,132,384 A | 10/2000 | Christopherson et al. | |
| 6,152,935 A | 11/2000 | Kammerer et al. | |
| 6,161,541 A | 12/2000 | Woodson | |
| 6,251,059 B1 | 6/2001 | Apple et al. | |
| 6,267,775 B1 | 7/2001 | Clerc et al. | |
| 6,408,851 B1 | 6/2002 | Karell | |
| 6,409,720 B1 | 6/2002 | Hissong et al. | |
| 6,439,238 B1 | 8/2002 | Brenzel et al. | |
| 6,458,079 B1 | 10/2002 | Cohn et al. | |
| 6,523,541 B2 | 2/2003 | Knudson et al. | |
| 6,546,936 B2 | 4/2003 | Knudson et al. | |
| 6,547,787 B1 | 4/2003 | Altman et al. | |
| 6,558,321 B1 | 5/2003 | Burd et al. | |
| 6,601,584 B2 | 8/2003 | Knudson et al. | |
| 6,610,065 B1 | 8/2003 | Branch et al. | |
| 6,618,627 B2 | 9/2003 | Lattner et al. | |
| 6,636,767 B1 | 10/2003 | Knudson et al. | |
| 6,636,769 B2 | 10/2003 | Govari et al. | |
| 6,742,524 B2 | 6/2004 | Knudson et al. | |
| 6,764,446 B2 | 7/2004 | Wolinsky et al. | |
| 6,921,401 B2 * | 7/2005 | Lerch | A61B 17/688 606/232 |
| 6,955,172 B2 | 10/2005 | Nelson et al. | |
| 7,146,981 B2 * | 12/2006 | Knudson et al. | 128/848 |
| 7,188,627 B2 | 3/2007 | Nelson et al. | |
| 7,237,554 B2 | 7/2007 | Conrad et al. | |
| 7,337,781 B2 | 3/2008 | Vassallo | |
| 2001/0050084 A1 | 12/2001 | Knudson et al. | |
| 2001/0050085 A1 | 12/2001 | Knudson | |
| 2001/0054428 A1 | 12/2001 | Knudson et al. | |
| 2002/0189622 A1 | 12/2002 | Cauthen, III et al. | |
| 2003/0069626 A1 | 4/2003 | Lattner et al. | |
| 2003/0093128 A1 | 5/2003 | Freed et al. | |
| 2003/0125743 A1 | 7/2003 | Roman et al. | |
| 2004/0045556 A1 | 3/2004 | Nelson et al. | |
| 2005/0004417 A1 | 1/2005 | Nelson et al. | |
| 2005/0092332 A1 | 5/2005 | Conrad et al. | |
| 2005/0092334 A1 | 5/2005 | Conrad et al. | |
| 2006/0201519 A1 | 9/2006 | Frazier et al. | |
| 2006/0207606 A1 | 9/2006 | Roue et al. | |
| 2006/0235264 A1 | 10/2006 | Vassallo | |
| 2007/0078430 A1 | 4/2007 | Adams | |
| 2007/0119463 A1 | 5/2007 | Nelson et al. | |
| 2007/0144534 A1 | 6/2007 | Mery et al. | |
| 2007/0144539 A1 | 6/2007 | van der Burg et al. | |
| 2007/0261701 A1 | 11/2007 | Sanders | |
| 2007/0288057 A1 | 12/2007 | Kuhnel | |
| 2008/0021485 A1 | 1/2008 | Catanese, III et al. | |
| 2008/0023012 A1 | 1/2008 | Dineen et al. | |
| 2008/0027560 A1 | 1/2008 | Jackson et al. | |
| 2008/0066766 A1 | 3/2008 | Paraschac et al. | |
| 2008/0066767 A1 | 3/2008 | Paraschac et al. | |
| 2008/0078412 A1 | 4/2008 | Buscemi et al. | |
| 2008/0139877 A1 | 6/2008 | Chu et al. | |
| 2009/0177027 A1 | 7/2009 | Gillis | |

FOREIGN PATENT DOCUMENTS

| | | |
|---|---|---|
| JP | 2001145646 A | 5/2001 |
| JP | 2008-526286 | 7/2008 |
| WO | 99/32057 | 7/1990 |
| WO | 92/21291 | 12/1992 |
| WO | 97/21385 | 6/1997 |
| WO | 99/00058 | 1/1999 |
| WO | 2000/029063 | 5/2000 |
| WO | 2003/092765 | 11/2003 |
| WO | 2004/064729 A2 | 8/2004 |
| WO | 2005/044158 A1 | 5/2005 |
| WO | 2005051292 A2 | 6/2005 |
| WO | 2005/082452 | 9/2005 |
| WO | 2005/110280 | 11/2005 |
| WO | 2007/064908 A2 | 6/2007 |
| WO | 2007/092865 | 8/2007 |

OTHER PUBLICATIONS

Michael Freidman et al., "Minimally Invasive Single-Stage Multi-level Treatment for Obstructive Sleep Apnea/Hypopnea Syndrome", The Laryngoscope (Oct. 2007)vol. 117, pp. 1859-1863.

Yosef P. Krespi et al., "Hyoid Suspension for Obstructive Sleep Apnea", Operative Techniques in Otolaryngology—Head and Neck Surgery (Jun. 2002), vol. 13, No. 2 , pp. 144-149.

Sheldon M. Mintz et al., "A Modified Geniotomy Technique for Obstructive Sleep Apnea Syndrome", J. Oral Maxillofac Surgery (1995), vol. 53, pp. 1226-1228.

Ståle Nordgård et al., "One-year Results: Palatal Implants for the Treatment of Obstructive Sleep Apnea", Otolaryngology—Head and Neck Surgery (2007), vol. 136, pp. 818-822.

Robert W. Riley et al., "Surgery and Obstructive Sleep Apnea: Long-Term Clinical Outcomes", Operative Techniques in Otolaryngology—Head and Neck Surgery (Mar. 2007), vol. 122, No. 3, pp. 415-421.

B. Tucker Woodson, "A Tongue Suspension Suture for Obstructive Sleep Apnea and Snorers", Operative Techniques in Otolaryngology—Head and Neck Surgery (Mar. 2001) vol. 124, No. 3, pp. 297-303.

B. Tucker Woodson, MD., et al., "A Randomized Trial of Temperature-Controlled Radiofrequency, continuous Positive Airway Pressure, and Placebo for Obstructive Sleep Apnea Syndrome", Otolaryngology—Head and Neck Surgery (Jun. 2003), vol. 128, No. 6, pp. 848-861.

B. Tucker Woodson, MD., et al., "Pharyngeal Suspension Suture with Repose bone Screw for Obstructive Sleep Apnea", Otolaryngology—Head and Neck Surgery (Mar. 2000), vol. 122, No. 3, pp. 395-401.

Doghramji, K., M.D. et al., *Predictors of Outcome for Uvulopalatopharnygoplasty*, Laryngoscope, vol. 105, pp. 311-314, 1995.

Horner, R., *Motor control of the Pharyngeal Musculature and Implications for the Pathogenesis of Obstructive Sleep Apnea*, Sleep, vol. 19, pp. 827-853, 1996.

Loube, D., M.D., *Technologic Advances in the Treatment of Obstructive Sleep Apnea Syndrome*, Chest, vol. 116, pp. 1426-1433, 1999.

Mickelson, S., M.D. et al., *Midline Glossectomy and Epiglottidectomy for Obstructive Sleep Apnea Syndrome*, Laryngoscope, vol. 107, pp. 614-619, 1997.

(56) References Cited

OTHER PUBLICATIONS

Powell, N., M.D. et al, *Radiofrequency Volumetric Tissue Reduction of the Palate in Subjects with Sleep-Disordered Breathing*, Chest, vol. 113, pp. 1163-1174, 1998.

Proffit, W., D.D.S., Ph.D., Muscle Pressures and Tooth Position: A Review of Current Research, Australian Orthodontic Journal, pp. 104-108, 1973.

Rotunda, A., M.D. et al., *Detergent Effects of Sodium Deoxycholate are a Major Feature of an Injectable Phosphatidylcholine Formulation Used for Localized Fat Dissolution*, Dermatologic Surgery, vol. 30(7), pp. 1001-1008, 2004.

Strollo, P. et al., Medical Therapy for Obstructive Sleep Apnea-Hypopnea Syndrome, *Principles and Practice of Sleep Medicine*, $4^{th}$ ed. pp. 1053-1065, 2005.

Treiber, E., M.D. et al., *Breast Deformity Produced by Morphea in a Young Girl*, Cutis, vol. 54, pp. 267-268, 1994.

Eugenio Vicente, MD., et al., "Tongue-Base Suspension in Conjunction with Uvulopalatopharyngoplasty for Treatment of Severe Obstructive Sleep Apnea; Long-Term Follow-Up Results," Laryngoscope (vol. 116); Jul. 2006, pp. 1223-1227.

Argamaso, "Glossopexy for Upper Airway Obstruction in Robin Sequence", Cleft Palate-Craniofacial Journal, May 1992, p. 232-238, vol. 29 No. 3.

Darrow et al., "Management of Sleep-Related Breathing Disorders in Children", Operative Techniques in Otolaryngology—Head and Neck Surgery, Jun. 2002, p. 111-118, vol. 13 No. 2.

De Lorenzi et al., "Glossopexy over tracheostomy in the treatment of glossoptosis", European Journal of Plastic Surgery, 2001, p. 25-27, vol. 24.

Fearon et al., "The Management of Long Term Airway Problems in Infants and Children", Ann Otol, 1971, p. 669-677, vol. 80.

Morgan et al, "Surgical Management of Macroglossia in Children", Archives of Otolaryngology—Head & Neck Surgery, Mar. 1996, p. 326-329, vol. 122.

Routledge, "The Pierre-Robin Syndrome: A Surgical Emergency in the Neonatal Period", British Journal of Plastic Surgery, 1960, p. 204-218, vol. 13.

International Search Report from PCT/2007/61721 (2 pgs.).

* cited by examiner

METHODS AND DEVICES FOR TREATING SLEEP APNEA AND SNORING

CROSS REFERENCE TO RELATED APPLICATIONS

This application is a continuation-in-part of U.S. patent application Ser. No. 10/597,590, filed Jul. 31, 2006, now U.S. Pat. No. 8,925,551 which is a national stage filing, under 35 U.S.C. § 371 of International Patent Application No. PCT/US2005/006430, filed Feb. 28, 2005, which claims the benefit of U.S. Provisional Patent Application No. 60/547,897, filed Feb. 26, 2004, all of which applications are hereby incorporated by reference herein. This application also claims the benefit of U.S. Provisional Patent Application No. 60/765,638, filed on Feb. 6, 2006, which application is hereby incorporated by reference herein.

FIELD OF THE INVENTION

This invention relates to methods and devices for maintaining upper airway patency.

BACKGROUND OF THE INVENTION

Snoring, upper airway resistance syndrome, and obstructive sleep apnea syndrome (OSAS) are all related to narrowing or obstruction of the upper airway during sleep (sleep disordered breathing). According to the National Institutes of Health (NIH), approximately 18 million Americans have sleep apnea (sleep disordered breathing), but fewer than 50% are presently being diagnosed. According to the National Highway Traffic and Safety Administration (NHTSA), 100,000 accidents and 1,500 traffic fatalities per year are related to drowsy driving. More than 50% of Americans over age 65 have sleep difficulties, and prevalence of sleep problems will therefore increase as the over-65 population increases. Each year, sleep disorders, sleep deprivation, and excessive daytime sleepiness add approximately $16 billion annually to the cost of health care in the U.S., and result in $50 billion annually in lost productivity.

Pathophysiology of Sleep Disorders

Sleep disorders are largely caused by too much soft tissue in the throat. Humans are unique because their upper airway has a curved shape, an anatomical change that is related to the evolution of human speech. As a result the upper airway of humans is more flexible than that of other species and is more prone to collapse under negative pressure. In the awake state a certain amount of tone is present in upper airway muscles to prevent this collapse. However, during sleep muscle tone decreases in upper airway muscles and in certain susceptible individuals this relaxation allows the airway to collapse (Homer R L. Motor control of the pharyngeal musculature and implications for the pathogenesis of obstructive sleep apnea. *Sleep* 1996; 19: 827-853).

The upper airway refers to the air filled spaces between the nose and the larynx (FIG. 1). The most relevant part of the upper airway for sleep disorders is the air cavity at the back of the throat called the pharynx. The pharynx can be divided into three anatomical levels (FIG. 2):

1) The nasopharynx is the part of the pharynx in the back of the nasal cavity.

2) The part at the back of the mouth is called the oropharynx. To be more precise it is best called the velopharynx. This level corresponds to that part of the pharynx containing the velum (soft palate) and tongue curve.

3) The hypopharynx is behind the tongue base.

The velopharynx is more susceptible to collapse because there are more soft tissue structures, leaving less room for airflow. The major structures of the velopharynx are the soft palate and the tongue, both of which are very flexible. The soft palate acts as a barrier between the mouth and the nose. In many people it is longer than necessary and extends down between the tongue and pharyngeal wall. The tongue is the largest muscular organ of the upper airway and is anatomically divisible into a blade, body and base (FIG. 3). Most of the tongue's curve is at the junction of the tongue body and base.

In the awake condition the structures of the velopharynx maintain their shape because of continuous tone of their internal muscles. When this tone decreases, such as during sleep, these structures become quite flexible and distensible. Without the normal muscle tone that keeps them in place, they tend to collapse at relatively low negative pressures. Although muscles relax throughout the body during sleep many of the respiratory muscles remain active. Specifically the major muscle that pulls the tongue forward, the genioglossus muscle, has been reported to show normal or increased activity during obstructive apneas. Normally the genioglossus is capable of moving the tongue forward and even projecting it out of the mouth. Why the genioglossus muscle sometimes fails to prevent obstructions has not been explained.

During inspiration the chest wall expands and causes negative pressure to draw air into the nose and mouth and past the pharynx into the lungs. This negative pressure causes upper airway soft tissue to deform, further narrowing the airway. If the airway narrows enough the air flow becomes turbulent causing the soft palate to vibrate. The vibration of the soft palate produces the sound known as snoring. Snoring is extremely common effecting up to 50% of men and 25% of women. By itself snoring is not a medical problem although it can be a tremendous problem for the patient's bed partner and a major cause of marital strain.

A small amount of decreased airflow or brief obstructions occur in all humans during sleep. These episodes are counted as medically significant if airflow is decreased more than 50% of normal (hypopnea) or if airflow is obstructed for more than 10 seconds (apnea). The number of apneas and hypopneas that occur during each hour of sleep is measured to diagnose the severity of the sleep disorder. These episodes of hypopnea or apnea often cause some degree of arousal during sleep. Although the patient does not awaken to full consciousness, the sleep pattern is disturbed causing the patient to feel sleepy during the day. If the frequency of hypopnea or apnea is more than 5 episodes an hour it is called upper airway resistance syndrome. These patients often show symptoms related to the sleep disruption. Specifically, these patients are excessively sleepy during the day. In addition more subtle symptoms such as depression and difficulty in concentrating are also commonly reported.

Technically the diagnosis of OSAS is defined as an average of more than 10 episodes of hypopnea or apnea during each hour of sleep. Although the airway is obstructed the patient makes repeated and progressively more forceful attempts at inspiration. These episodes are silent and characterized by movements of the abdomen and chest wall as the patient strains to bring air into the lungs. Episodes of apnea can last a minute or more, and during this time the oxygen levels in the blood decrease. Finally, either the obstruction is overcome, usually producing a loud snore, or the patient awakes with the feeling of choking.

Very common symptoms in OSAS patients are morning headaches and acid reflux. During airway obstructions the forceful attempts to inspire air can cause tremendous negative pressure in the chest. These high negative pressures can draw acid up the esophagus from the stomach. The acid can travel all the way into the mouth and cause inflammation of the vocal cords and nasal mucosa. The presence of the acid in the upper airway causes reflex bronchoconstriction in the lung that is similar to an asthma attack. If even a small amount of acid enters the lung it can cause the vocal folds to close tightly and itself cause a prolonged apnea called laryngospasm. In many patients the repeated stretching of the espophageal sphincter causes chronic changes and these patients can have acid reflux during the day.

Most importantly, sleep disorders can cause serious medical disorders and death. Apneas cause a large strain on the heart and lungs. Over time the many repeated episodes of apnea cause chronic changes leading to hypertension. Long periods of apnea allow the oxygen levels in the blood to decrease. In turn the low oxygen can cause heart attacks or strokes.

Treatment of Sleep Disorders

Although OSAS occurs in both children and adults the cause and treatment is very different. OSAS in children almost always occurs when the child has large tonsils, and tonsillectomy cures the condition. Tonsils naturally decrease in size with age and are rarely a problem in adults. Instead susceptible adults usually have enlargement of their tongues, soft palate and/or pharyngeal walls. This enlargement is mostly due to fat deposits within these structures.

Adult sleep disorders are difficult to treat for a variety of reasons. The upper airway is a very mobile structure that performs the critical functions of swallowing and speech. These functions are easily compromised by surgical procedures or other interventions. In addition, the upper airway also has a large amount of sensory innervation that causes reflex gagging and coughing. Theoretically a physical stent that is placed in the oral cavity and pharynx would be completely effective in relieving sleep apnea. When a patient is totally unconscious, such as when they are anesthetized for surgery, the airway can be stented open by placing a curved oral tube into the mouth and pharynx. In addition, endotracheal tubes establish a secure airway for artificial ventilation. However, after anesthesia wears off, patients immediately sense and react to the foreign objects in their throats and expel them. Therefore devices such as oral and endotracheal tubes, or anything similar, cannot be used for the treatment of OSAS.

Although physical stents cannot be used for OSAS an indirect way of stenting the upper airway with positive air pressure is the most common prescribed treatment for OSAS. This method is called continuous positive airway pressure (CPAP). CPAP requires the use of a mask tightly attached around the nose and connected to a respirator. The exact amount of positive pressure is different for each patient and must be set by overnight testing using multiple pressures. The positive pressure acts like a stent to keep the airway open. CPAP is not a cure but a therapy that must be used every night. Although many OSAS patients are helped by CPAP it is not comfortable for the patient or their bed partner. Patients often cannot tolerate the claustrophobic feeling of a mask tightly attached to their face. In addition there are often many technical problems with maintaining a proper seal of the mask to the face. For these reasons up to half of all patients who are prescribed CPAP stop using it within 6 months (Sanders, "Medical Therapy for Sleep Apnea," Principles and Practice of Sleep Medicine, 2nd Edition, pp. 678-684).

Tracheotomy

The only completely effective surgical therapy for OSAS is to bypass the entire upper airway by performing a permanent tracheotomy, a surgical procedure that forms a direct connection to the trachea through the neck. This is a dangerous procedure reserved for the worst cases when there is a high risk of serious medical complications from OSAS. Notably, temporary tracheotomies are often performed on patients with severe OSAS to control the airway before any other procedure is performed on their upper airway. The reason is that these patients are at high risk of acute airway obstruction and death if there is any swelling in their airways. Due to the tremendous excess of swollen tissue in their upper airways OSAS patients are very difficult to intubate under emergency conditions. Similarly there is tremendous amount of fat in the neck that makes emergency tracheotomies extremely hazardous.

Prior to current conservative measures, post operative deaths were not uncommon in severe OSAS patients. Moreover these patients often have acclimated to breathing against resistance, and when the resistance is suddenly removed their respiratory drive decreases. Even today the standard of care in treating most OSAS patients is to have them under close observation in an intensive care unit or recovery room after surgical procedures.

Soft Palate Procedures for Snoring

As the soft palate vibrates more than other tissues it plays a disproportional role in snoring. Various surgical therapies are available that shrink or stiffen the soft palate. The main procedure used is called uvulopalatopharyngoplasty (UPPP). UPPP excises excess soft tissue of the pharyngeal walls and soft palate with a surgical scalpel Because so much mucosa of the pharyngeal area is traumatized during a UPPP there is a large amount of post operative swelling and severe pain. In selected patients who snore but have no obstructions more limited versions of the UPPP can be done with lasers or electrical cautery.

Newer procedures minimize trauma to the mucosa and use needles to reach the underlying soft tissue to shrink its volume or stiffen it so that it resists vibration. Electrodes can be inserted into the soft palate to deliver radiofrequency energy that shrinks or stiffens the palate (Powell, N B, et al (1998) Radiofrequency volumetric tissue reduction of the palate in subjects with sleep-disordered breathing. Chest 113, 1163-1174.) (Somnoplasty; Somnus; Mountainview, Calif.). Mild caustic agents can be injected that decrease the volume of the soft palate. U.S. Pat. No. 6,439,238 to Benzel teaches the application of a stiffening agent to the surface of the soft palate. Most recently, office based implantation of plastic inserts to stiffen the soft palate has been approved by the FDA (Pillar® Procedure, U.S. Pat. No. 6,546,936: Method and apparatus to treat conditions of the nasopharyngeal area).

The fundamental shortcoming of all procedures that target the soft palate, including the newer techniques, is that they only partially improve OSAS (Loube D I (1999) Technologic Advances in the Treatment of Obstructive Sleep Apnea Syndrome. Chest. 1999; 116:1426-1433, Doghramji, K, et al (1995) Predictors of outcome for uvulopalatopharyngoplasty. Laryngoscope 105, 311-314). Although studies report a decrease in the number of apneas these patients are rarely cured. Evidently the critical structure causing OSAS is not the soft palate but the tongue.

Tongue Base Procedures for OSAS

The methods used to treat the tongue base in OSAS are either to permanently decrease its volume, to decrease its flexibility or to move the entire tongue forward.

Surgical excision of the tongue base has been poorly effective. The results for scalpel or laser resection of the tongue base in OSAS treatment have not been good enough to recommend continued application of these procedures (Mickelson, S A, Rosenthal, L (1997). Midline glossectomy and epiglottidectomy for obstructive sleep apnea syndrome. Laryngoscope 107, 614-619).

More recently radiofrequency (U.S. Pat. No. 5,843,021 to Edwards) and ultrasonic (U.S. Pat. No. 6,409,720) energy have been proposed to shrink and stiffen the tongue base with radiofrequency energy. The radiofrequency energy is delivered via needle electrodes that are inserted into the tongue base to cause a lesion that scars and shrinks over time. To avoid postoperative swelling and pain a limited amount of lesioning is done in a single session and patients require an average of 5 treatments. About a third of patients have greater than 50% improvement in their OSAS. However, approximately a fourth of patients have significant post operative complications, including, tongue base ulceration and abscesses, and temporary tracheotomy.

A recent introduced device for tongue base advancement is the Repose® system (Influent Corp; San Francisco, Calif.). The Repose® procedure is performed under general anesthesia, and a screw is inserted at the base of the mandible. The screw contains attachments for a permanent suture that is tunneled under the mucosa of the floor of the mouth to the back of the tongue, then passed across the width of the tongue base, and brought back to attach to a metal hook screwed into the bone of the mandible. The suture is tightened to displace the tongue base forward, and caution must be observed to prevent excess tension leading to necrosis of tissue. Unfortunately studies of the Repose® procedure show that it is ineffective at eliminating OSAS. Only 1 of 15 patients was cured of OSAS while 2 patients had to have the suture removed due to pain and swelling.

More aggressive surgical procedures require reconstruction of the mandible, facial, skeleton or the hyoid bone. An example of the art is U.S. Pat. No. 6,161,541 to Woodson that teaches a method of surgically expanding the pharyngeal airway. These procedures require extensive surgery with higher risks and much longer recovery periods.

Other proposed methods for treating the tongue base include stiffening the soft tissue by injection of sclerosing particles U.S. Pat. No. 6,742,524 or other implanted material U.S. Patent Application Publication No. 20050004417A1.
Neuroprosthetic Devices Various neuroprosthetic devices have been invented that stimulate upper airway muscles. U.S. Pat. No. 4,907,602 to Sanders describes transmucosal stimulation to dilate the airway; U.S. Pat. No. 5,792,067 to Karell teaches an intraoral device that applies electrical stimulation to the hard palate, soft palate or pharyngeal area to induce contraction of the upper airway muscles; U.S. Pat. No. 5,190,053 to Meer teaches an intraoral device that applies electrical stimulation to the genioglossus muscle via electrodes located on the mucosa on the floor of the mouth on either side of the frenulum. In addition U.S. Pat. No. 5,591,216 to Testerman describes a totally implantable device to stimulate the nerves to the genioglossus muscles. In addition, WIPO Publication No. 04064729 to Gordon describes a neuroprosthetic device that can be injected into the soft palate to treat snoring. At present these devices have not been clinically proven.

In summary, sleep disorders are a significant health problem without an acceptable solution and there is a need in the art for new and more effective therapies.

While not wishing to be bound by theory my studies of human tongue anatomy suggest that episodes of obstruction evolve by a sequence of events (FIG. 4). The initial inciting event is the deformation of a relatively small part of the tongue. Under certain conditions deformation begins in soft tissue on the top of the tongue, particularly in the area of the tongue curve, and specifically near the center line of the tongue curve. As this tissue deforms it narrows the airway and causes more negative pressure thereby causing greater deformation. This feedback cycle in turn deforms enough tissue in the area to cause a complete obstruction in the velopharyngeal area.

If an initial obstruction occurs near the end of inspiration, the obstruction is relieved by an expiration, or by action of the genioglossus muscle. However, if the obstruction occurs at the beginning of inspiration reflexes trigger stronger inspiratory effort that further lowers airway pressure. This increased negative pressure causes deformation and collapse of most of the tongue base. At this point the airway is firmly plugged by soft tissue and activity of the genioglossus only stretches the tongue tissue that is plugged and cannot dislodge it.

Therefore the tongue curve is the critical area that initiates the cascade leading to obstruction. This relaxed muscle is very flexible and easy to deform, however, the converse is also true, very little force is needed to prevent this deformation. Therefore if sufficient counterforce is exerted at the proper localized area of the tongue it can prevent obstruction without noticeable effects on speech and swallowing movements.

How a device could prevent the deformation and collapse of the tongue curve is not a trivial problem:
  This area of the tongue is very mobile during speech and swallowing, therefore the amount of force exerted must be low and highly localized. It is unacceptable to render the area immobile, as would be done if were stiffened by a large implant or scar tissue,
  The whole area of the velopharynx has extensive sensory innervation, and relatively minor stimulation there causes either a gag or a swallow.
  The tongue base and body have a larger blood supply than comparable muscles elsewhere in the body. Any implant placed in the area has a high probability of causing internal bleeding with potentially catastrophic tongue swelling.
  Soft tissue and tongue in particular remodel easily. Specifically sutures or implants that exert force cause the tissue to remodel to relieve that force. This is known as the cheese cutter effect. Therefore the forces applied must be relatively low and applied for limited periods.
  Humans' upper airway anatomy is highly variable, and the pathological anatomy of sleep apnea patients is even more variable. Moreover the upper airway anatomy of sleep apnea patients changes over time as the disease progresses or improves.
  Finally, OSAS patients have borderline airways that can obstruct after even minor amounts of swelling such as that following surgical manipulation. Therefore it is not obvious how a device could both exert force in the area yet avoid swelling.

Moreover to be maximally effective and get patient and physician acceptance the device would ideally require additional qualities:
  It should be capable of being inserted as an outpatient procedure.
  Preferably the device could he removed during the day and reinserted by the patient at night.

It would be adjustable to conform to the specific needs of the patient.

It would be comfortable for the patient.

When the device was in place it would not be noticeable to anyone else.

SUMMARY OF THE INVENTION

There is a tremendous variability in human upper airway anatomy, and even further variation in the pathological changes contributing to sleep apnea and related disorders. Moreover, the pathological anatomy changes over time in each patient as their condition improves or deteriorates. No single method and device is able to treat all contingencies. Therefore there is a critical need for methods and devices that are optimized for different sites in the upper airway.

Embodiments of the invention include methods and devices to prevent or treat upper airway disorders in mammals related to impaired airflow. These disorders are, without limitation, snoring, upper airway resistance syndrome, and obstructive sleep apnea. In addition, this invention is applicable to airway disorders in animals including but not limited to dorsal displacement of the soft palate in horses and brachycephlic obstructive airway syndrome in certain breeds of dog. Those skilled in the art will readily appreciate that application of this invention can be applied to other conditions of the upper airway.

One aspect of the invention prevents airway obstruction by dilating the airway or preventing the tissue from deforming. It enlarges the airway when excess tissue is present and also counteracts the deforming influence of negative airway pressure on the relaxed soft tissue of upper airway structures. These structures include, without limitation, the tongue, soft palate, pharyngeal walls and supraglottic larynx.

PCT Publication No. WO 2005/082452 describes one embodiment of the method and device herein referred to as a Linguaflex tongue retractor (LTR), notwithstanding that the use of the device as disclosed herein is not limited to the tongue or to retraction. The LTR consists of a retractor (R), a shaft (S), and an anchor (A). In a preferred embodiment a retractor is physically coupled to the soft tissue of the tongue base. The shaft passes through the midline of the tongue to connect with an anchor. The anchor imparts counterforce through the shaft to the retractor, thereby preventing deformation of the soft tissue.

One aspect of this invention describes improvements to the retractor head, shaft and anchor that increase the efficacy of the device while decreasing patient discomfort. Improvements of the LTR components include but are not limited to a retractor head that collapses to fit within a narrow delivery device and expands after insertion; a shaft that passively adjusts its length and tension in response to surrounding tongue activity; and a modified anchor that is adjustable by the patient and attaches to a soft bolster, a partially implanted receptacle in the mouth, and/or a dental appliance.

One aspect of the invention is a method of making the implant more comfortable by allowing the device to be under little or no tension during the day, the unloaded state, and to increase the tension to therapeutic levels at night, the loaded state. This method increases the comfort for the patient and allows the patient a large degree of control. The method and the devices that implement the method are of great importance as the lack of patient compliance is perhaps the largest problem with current sleep apnea therapies.

Another aspect of this invention is that additional sites in and around the tongue can unexpectedly be treated with this invention to prevent airway disorders. Non-limiting examples of these sites are the base of tongue, the mucosa covering the tongue, the tongue frenulum, the pharyngoglossal, palatoglossal and aryepiglottic folds, the lateral pharyngeal wall and soft palate. An improved LTR applied to these sites directly or indirectly stiffens and displaces the tongue base, soft palate and lateral pharyngeal walls and enlarges the velopharynx. Each site has specific anatomy for which novel and unexpected improvements to the LTR allow it to perform efficiently with minimal risk and discomfort to the patient.

One aspect of this invention is an LTR that indirectly retracts tongue base by its implant site in the frenulum area. This simplifies the insertion, adjustment and maintenance of the device.

Another aspect of this invention describes a highly localized and fully implantable LTR that is inserted into the base of the tongue to stiffen lax surface mucosa or mechanically couple it to internal tongue structures.

Another aspect of this invention is an LTR inserted in or around the pharyngoglossal fold. This site allows retraction and stiffening of tongue base tissue as well as the soft palate and lateral pharyngeal wall. The advantage of this site is its minimal invasiveness, safety and its beneficial effect on multiple different structures.

Another aspect of this invention is a method and device to remodel upper airway tissue in order to enlarge the pharyngeal airspace. Tissues remodeled include but are not limited to tongue base, palatine tonsil, pharyngeal wall and soft palate. Preferably these tissues are either compressed to decrease their volume, or displaced or reshaped. This effect lasts months to years after the devices have been removed. To achieve this persistent beneficial effect, devices would preferably exert force preferably from 1 week to 1 year, more preferably for 1 to 6 months.

Another aspect of this invention are non-invasive methods and devices that reversibly couple to mucosa to grasp, move and/or reposition soft tissue using magnets, adhesives, vacuum, and/or mechanical leverage. In one embodiment a curved retractor member is reversibly inserted into selected sites. In another embodiment indwelling clips are placed on the PGF, tonsillar folds, soft palate and other soft tissue folds. These retractor members can be loaded as needed by coupling them to modified anchors in or outside the mouth. In still another embodiment the floor of mouth is protracted to displace the tongue base. In a still further embodiment a vacuum reshapes the tongue to decrease base of tongue volume.

Another aspect of this invention describes LTRs specifically adapted to prevent dorsal displacement of the soft palate in horses.

In each site the LTR has multiple embodiments. The LTR can pass through tissue and have its retractor or anchor ends outside of tissue, or have only one end exposed, or the entire device can be implanted. The shaft of the device can pass deeply into the tissue, or pass superficially just beneath the mucosa. The retractor and anchor member is preferably shaped to fit its site so as to distribute force evenly: flat for flat or mildly curved surfaces such as the mid tongue base, pharyngeal wall, and soft palate; wedge shaped for the depths of the pharyngoglossal fold and lateral margin of the soft palate; V shaped for the frenulum; and T shaped for the teeth. The materials of the implant, retractor and anchor could be of any of the well known non-reactive biocompatible materials known in the art. Non-limiting examples of rigid materials include stainless steel, titanium, ceramics, and plastics. Elastomeric materials include silicon and rubber. The force needed to displace the tongue anteriorly or the soft palate superiorly varies from 0.001 gram to 10,000 grams. More preferable 0.1 gram to 1000 grams, most preferably 10-100 grams. This force could be applied from 0.01 sec to permanently. More preferable one minute to 1 month. Even more preferably for the duration of sleep. Most preferably during episodes of restricted upper airway flow.

BRIEF DESCRIPTION OF THE DRAWINGS

The present invention will be more readily understood from the detailed description of exemplary embodiments presented below considered in conjunction with the attached drawings, of which.

It is to be understood that the attached drawings are for purposes of illustrating the concepts of the invention.

DETAILED DESCRIPTION OF THE DRAWINGS

Figure 1:
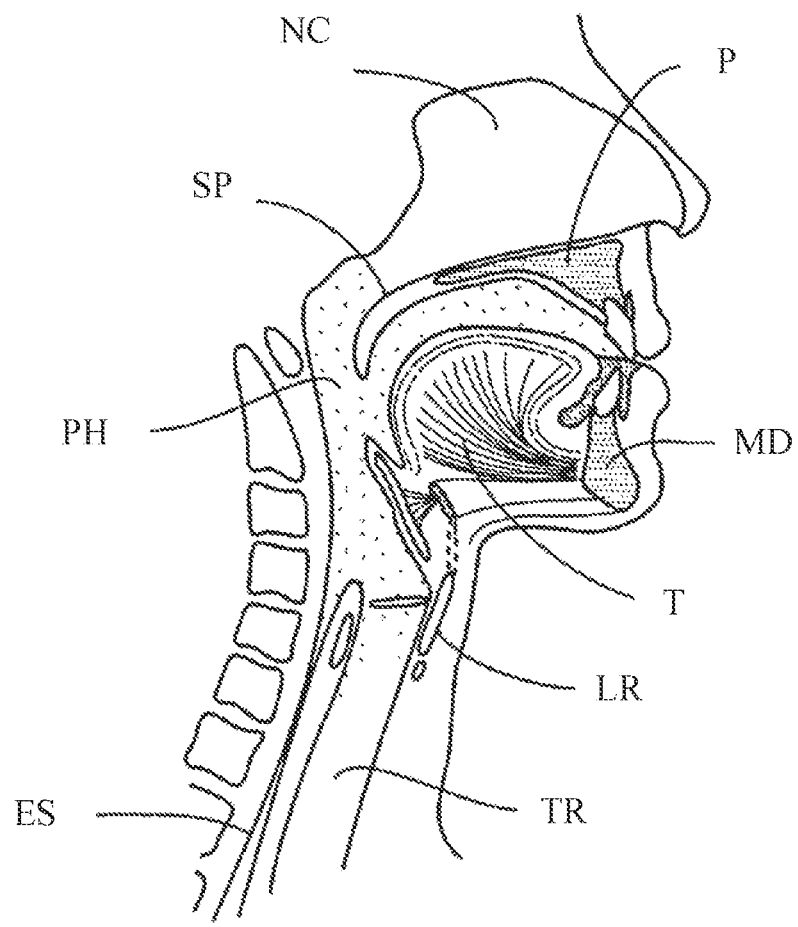
FIG. 1 is a drawing of the human upper airway in the mid saggital plane.
Figure 2:
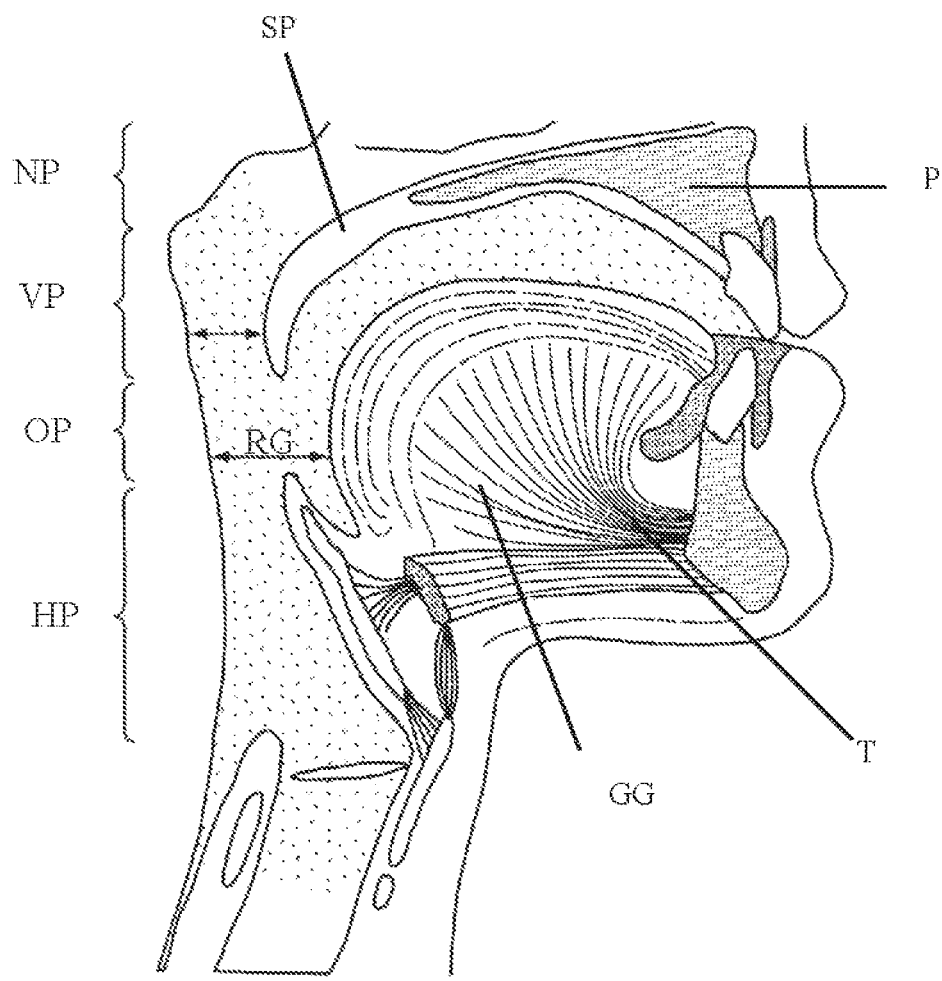
FIG. 2 is a simplified schematic drawing of the tongue and surrounding structures.

FIG. 1. Drawing of the Human Upper Airway in the Mid Saggital Plane.
NC, Nasal Cavity
SP, Soft Palate
PH, Pharynx
ES, Esophagus
P, Hard Palate
MD, Mandible
T, Tongue
LR, Larynx
TR, Trachea FIG. 2. Simplified Schematic Drawing of the Tongue and Surrounding Structures
 NP, Nasopharynx
 VP, Velopharynx
 HP, Hypopharynx
 SP, Soft palate
 P, Hard palate
 T, Tongue
 GG, Genioglossus muscle
 OP, Oropharynx
 RG, retroglossal space Areas of the pharynx: Nasopharynx spans from the level of the hard palate up. Velopharynx spans from the beginning of the end of the soft palate. Oropharynx spans from the edge of the soft palate to the epiglottis. Hypopharynx spans from the epiglottis to the esophagus. The velopharyngeal space (VP) is the area between the soft palate and back wall of the pharynx. The retroglossal space (RG) is the area between the tongue base and back wall of the pharynx.

Figure 3:
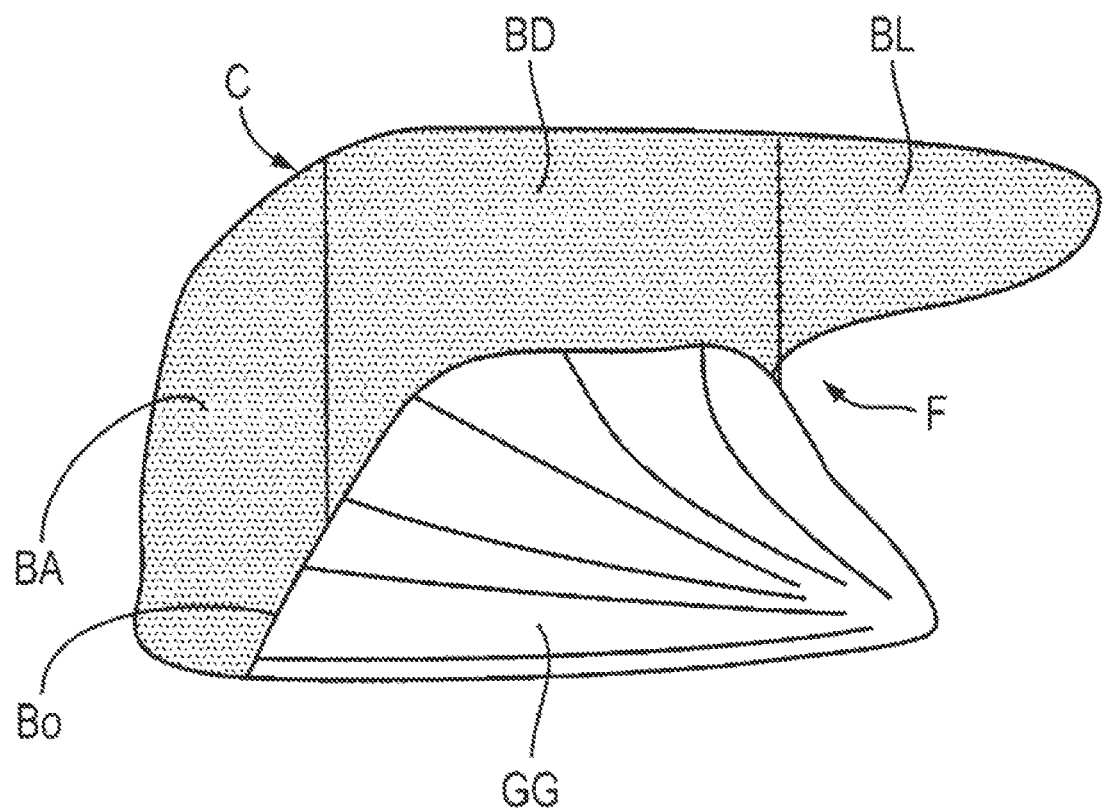
FIG. 3 illustrates Anatomical landmarks of the tongue.
Figure 4:
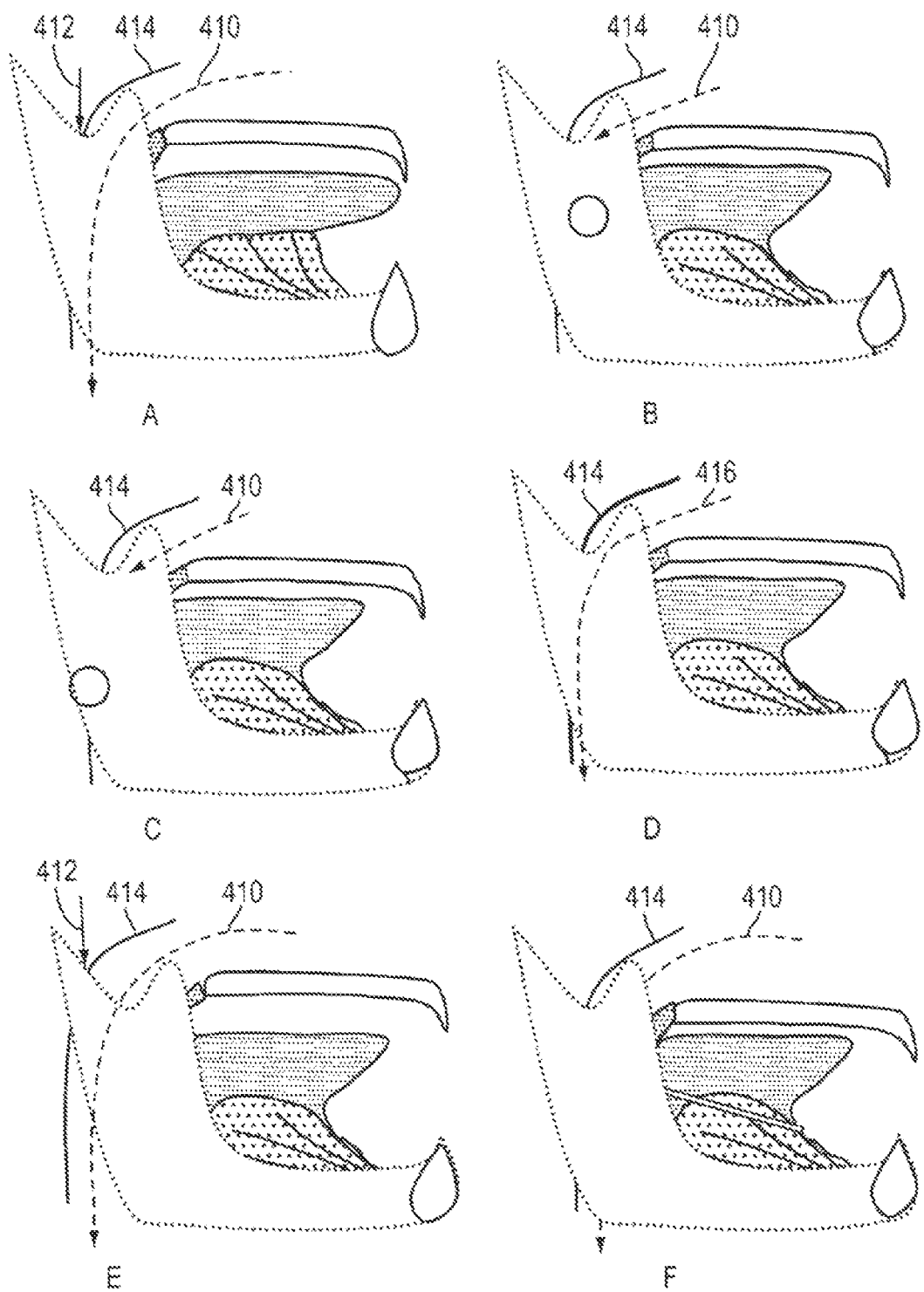
FIGS. 4A-4F illustrate a Mechanism of airway obstruction and the effect of current therapies.

FIG. 3. Anatomical landmarks of the tongue. The tongue will be defined as the grey area of this schematic. From front to back the tongue is divided into a blade, body, and base. The genioglossus muscle (GG) inserts into a connective tissue boundary on the undersurface of the tongue (Bo). The entire region of the genioglossus muscle and its mucosa is referred to as the "frenulum area".
 BA) Tongue base
 BD) Tongue body
 BL) Tongue blade
 Bo) Boundary between tongue and genioglossus
 C) Tongue curve
 F) Frenulum
 GG) Genioglossus muscle FIG. 4. Mechanism of Airway Obstruction and the Effect of Current Therapies.

A) Normal tone in tongue while awake. Tongue remains in position allowing airway to remain open. Blue arrow 410 shows airflow, small black arrow 412 shows the relationship of pharyngeal wall (red line 414) to mandible.

B) Apnea. During sleep muscle tone is lost in the tongue and it becomes flaccid. Negative pressure in the pharynx during inspiration causes backward collapse of the tongue in the velopharyngeal area because the airway is narrowest at that point and the tongue curve (circle) is most deformable.

C) Apnea. After the airway obstructs at the velopharyngeal area inspiration lowers the pressure in the pharynx further causing the base of tongue to deform and firmly block the airway.

D) CPAP works by pumping air at high pressure through the nose (thick blue line 416), thereby splinting the pharynx open.

E) Dental devices work by moving the entire jaw forward. As the tongue is attached to the soft tissues along the floor of the mouth, and they attach to the jaw, the tongue is indirectly moved to expand the airway. Note that the jaw has moved in relation to the pharyngeal wall (arrow).

F) The LTR prevents posterior deformation of the tongue curve by directly restraining the tongue curve from moving backwards.

Figure 5:
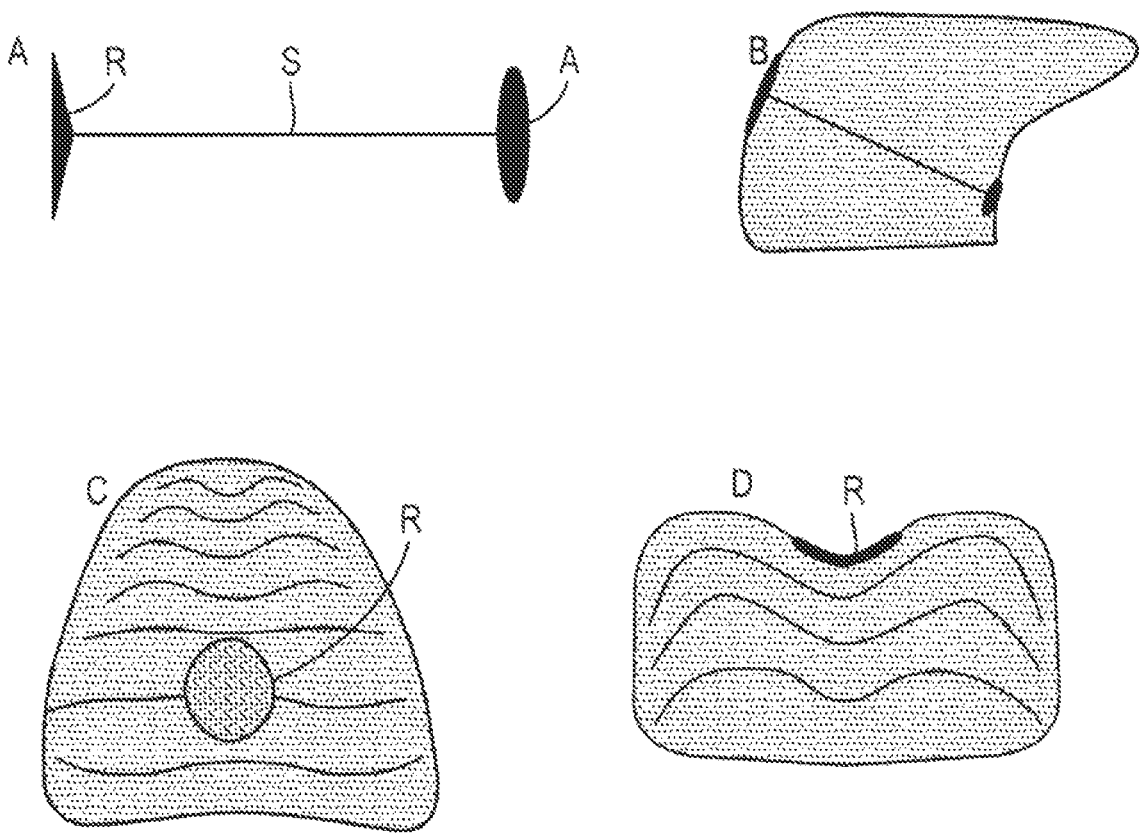
FIGS. 5A-5D illustrate an Embodiment of an LTR device.

FIG. 5. Embodiment of the LTR Device. Shown is One Embodiment of the LTR.

A. The LTR has three main components: a retractor (R), shaft (S), and anchor (A).

B. Side view of the LTR inserted in a tongue.

C. Back view of tongue curve showing retractor position.

D. Back view of tongue base showing the curved midline shape.

Figure 6:
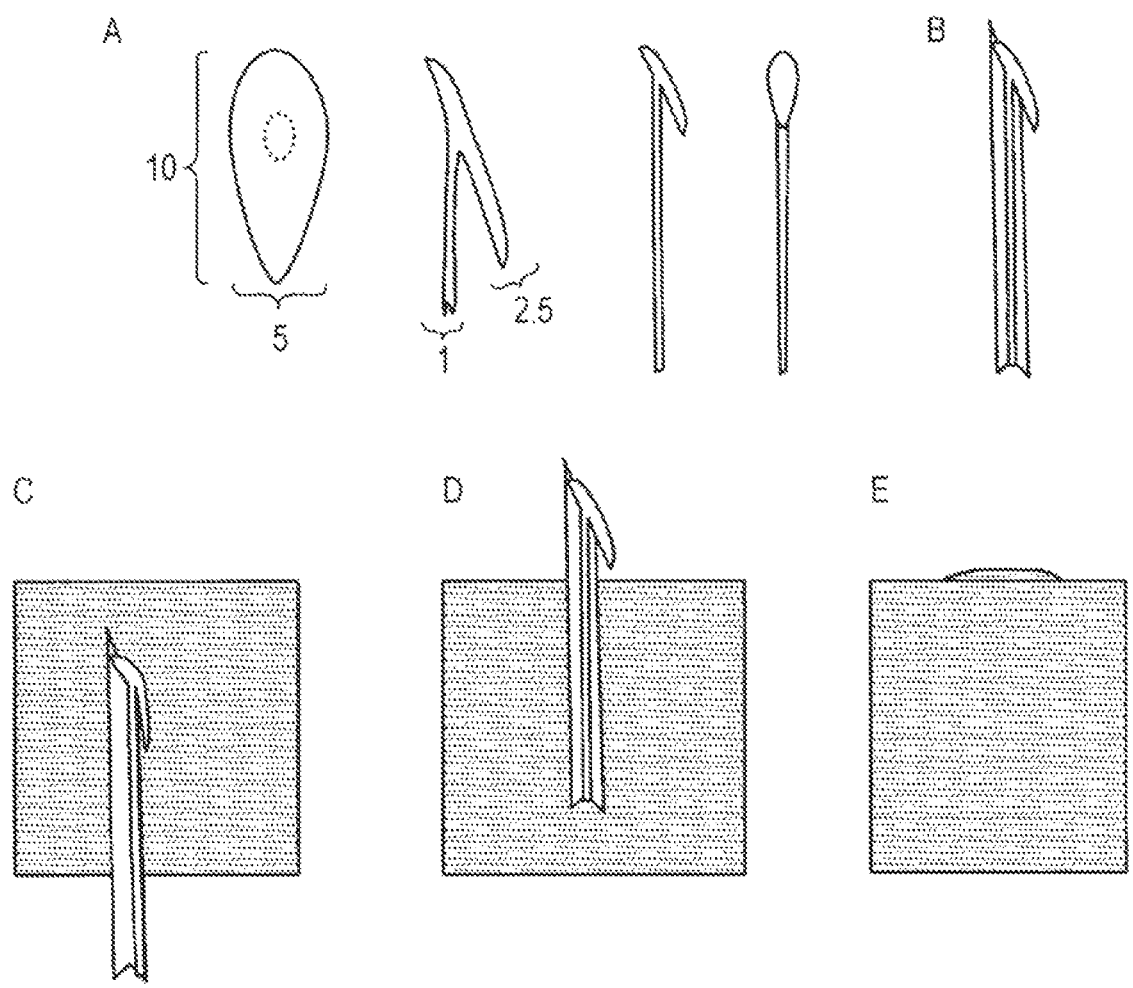
FIGS. 6A-6E illustrate a Retractor member.

FIG. 6. Retractor member. This figure illustrates a retractor component of an LTR that can be mounted on a needle for implantation within upper airway tissue and deploys when the needle is withdrawn. The retractor is shown as an integral component of the shaft and is molded as one piece from soft elastomeric material.

A. Side and front views of the retractor head. The plane of the retractor rests at about 15° relative to the shaft.

B. Side view of retractor head mounted within a needle. A part of the retractor lays on the outer surface of the needle.

C. Side view of needle passing through tissue. Note that the retractor extension lays flat against the needle barrel and does not interfere with passage of the needle through tissue.

D. After the needle penetrates mucosa enough to clear the retractor extension it again extends away from the shaft.

E. Slight traction on the shaft causes the retractor to catch the mucosa and come to rest in its working position.

Figure 7:
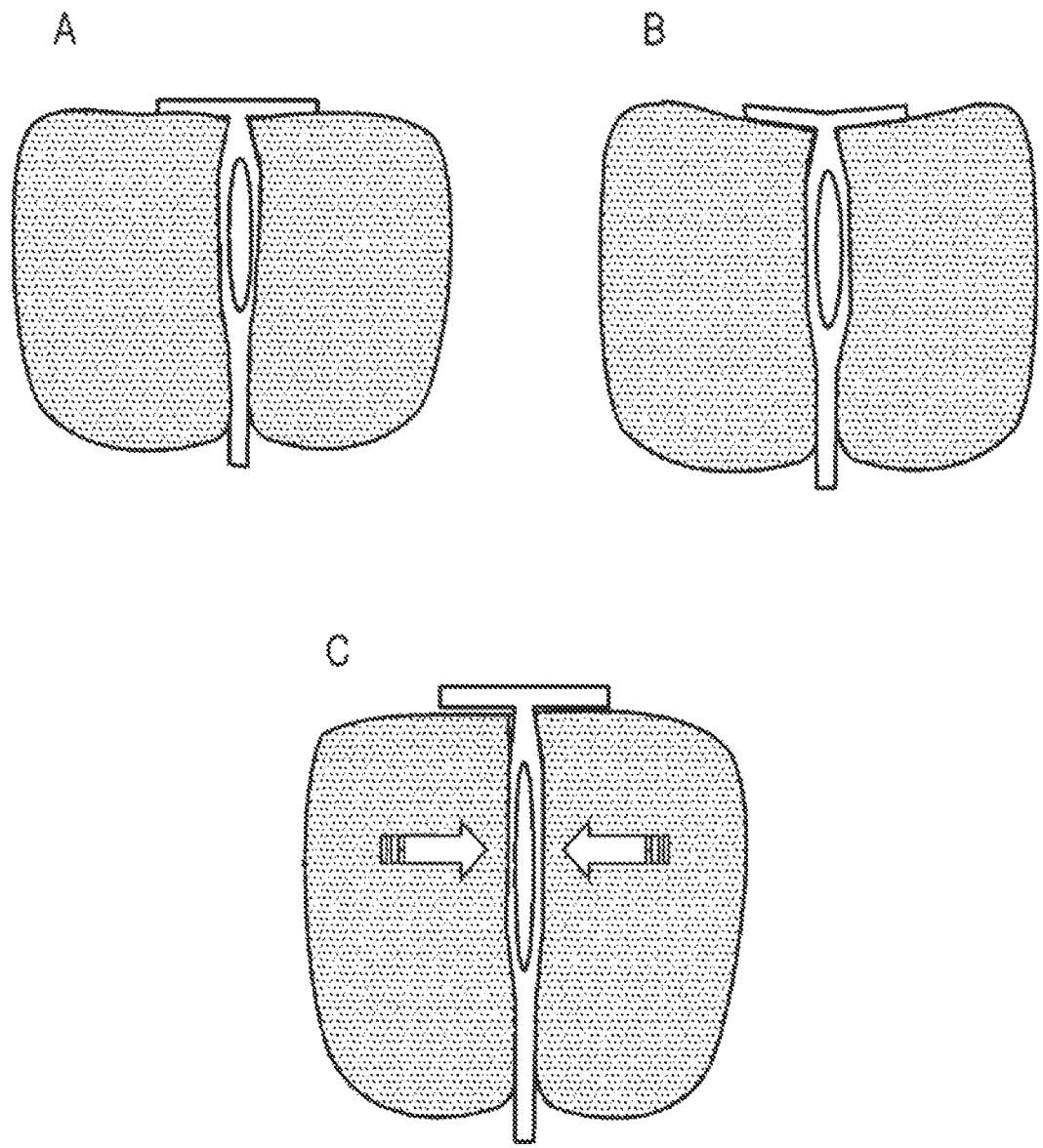
FIGS. 7A-7C illustrate a Shaft member.

FIG. 7. Shaft member. Shown is an improvement to the shaft of an LTR that maintains its retractor tension when the tongue is relaxed, such as during sleep. However, during speech and swallowing, when the tongue base often moves backward, the activity of the tongue squeezes the shaft and thereby lengthens it. In this way there is little or no resistance to the normal tongue movements.

A. Schematic view of LTR in the tongue with normal muscle tone. Note that the retractor lays on the mucosal surface of the tongue base without indenting it.

B. During sleep the tongue loses all tone and tends to flop backward into the airway. The retractor then resists this deformation.

C. During swallowing and speech the tongue base sometimes moves backward. During these movements there is a strong contraction of the tongue muscles. This contraction squeezes the upper shaft, this in turn causes the shaft to lengthen and move the retractor.

Figure 8:
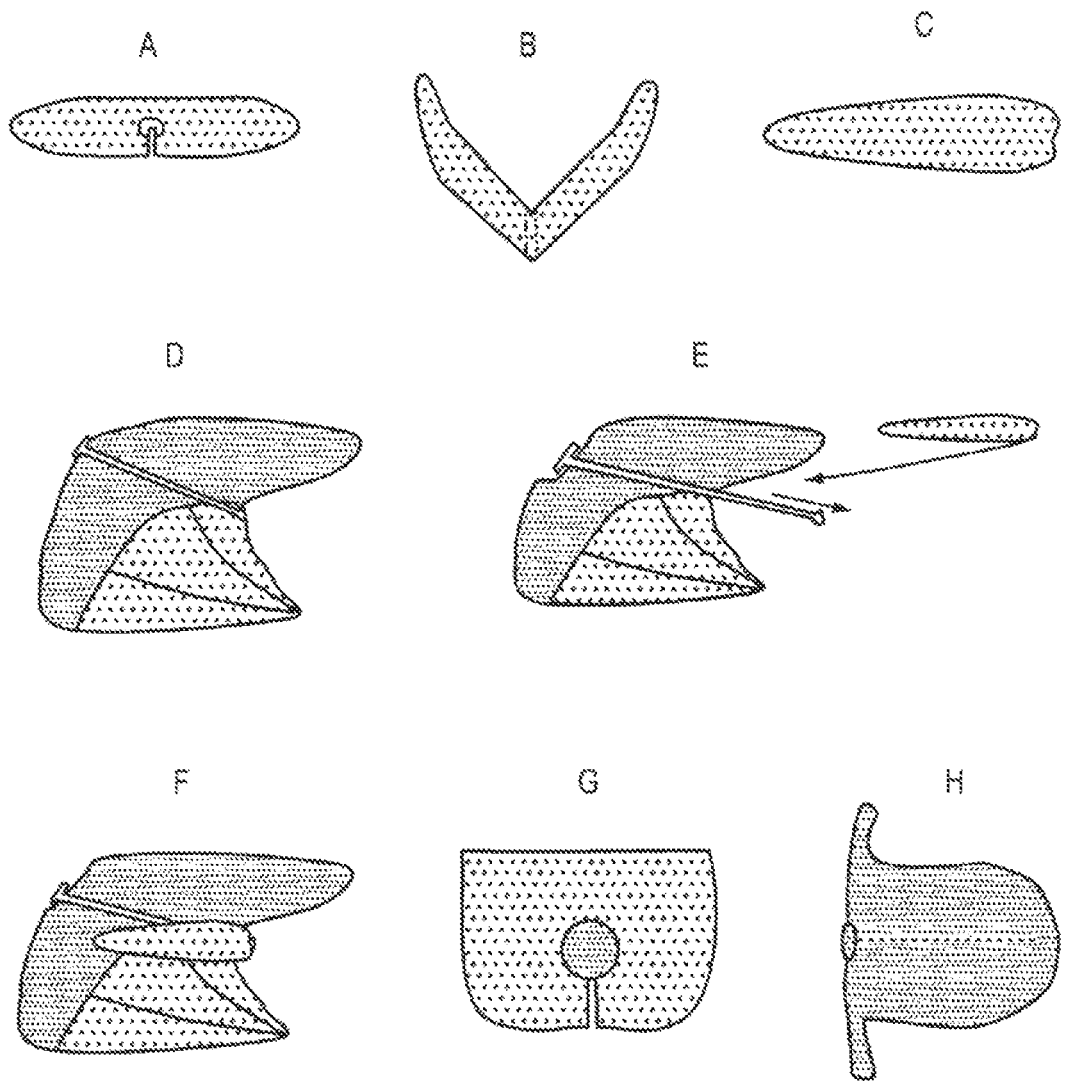
FIGS. 8A-8H illustrate an Anchor member, bolster.

FIG. 8. Anchor Member, Bolster
A. Front view of bolster.
B. Top view of bolster.
C. Side view of bolster.
D. Side view of tongue with unloaded LTR.
E. Anchor of shaft is pulled forward slotted into cleft on underside of bolster.
F. Bolster in position under tongue.
G. Close up view of LTR anchor sitting in the recess of bolster.
H. Top view of tongue with LTR and bolster.

Figure 9:
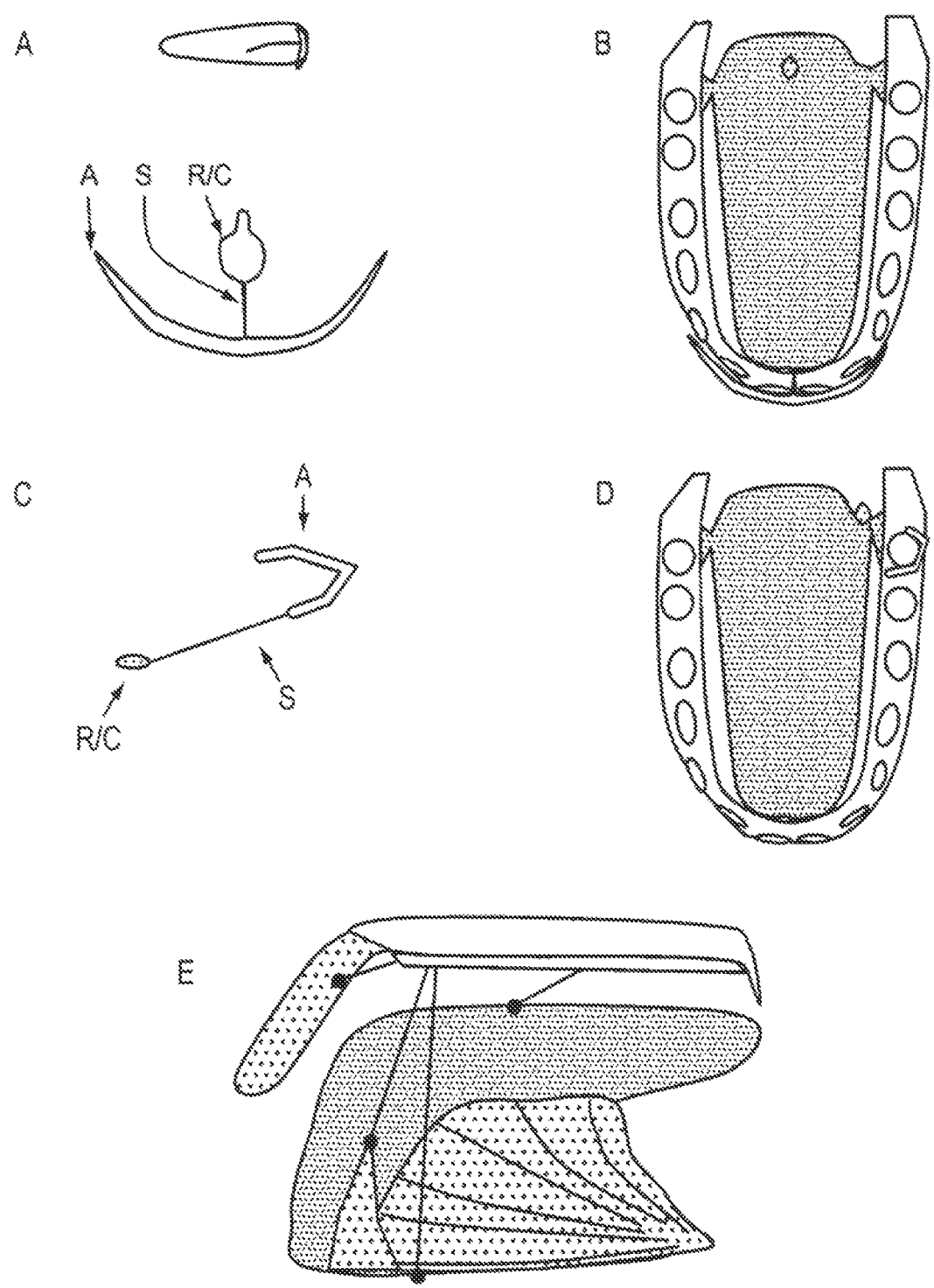
FIGS. 9A-9E illustrate an Anchor member, dental.

FIG. 9. Anchor Member, Dental
A. A modified anchor that is implanted on the upper or lower front teeth. The anchor (A) interfaces with the teeth, the shaft (S) connects to retractor/coupler (R/C). The retractor/coupler either consists of a retractor that interfaces with tissue, or a coupler component that connects to an implanted retractor, shaft, or anchor member of an implanted LTR.

B. Drawing of top view of tongue and mandible with an LTR implanted from the tongue base to the frenulum. The anchor of the LTR can be reversibly attached to the R/C component of the dental anchor.

C. Another embodiment of a modified anchor for use on the lateral teeth.

D. Top view of tongue and mandible with a lateral dental anchor. The anchor attaches to the molar tooth, the shaft passes through the pharyngoglossal fold, and the retractor rests against the posterior surface of the fold.

E. Palatal prosthesis with some possible coupling extensions for retraction or protraction: the soft palate, PGF, floor of mouth and tongue surface.

Figure 10:
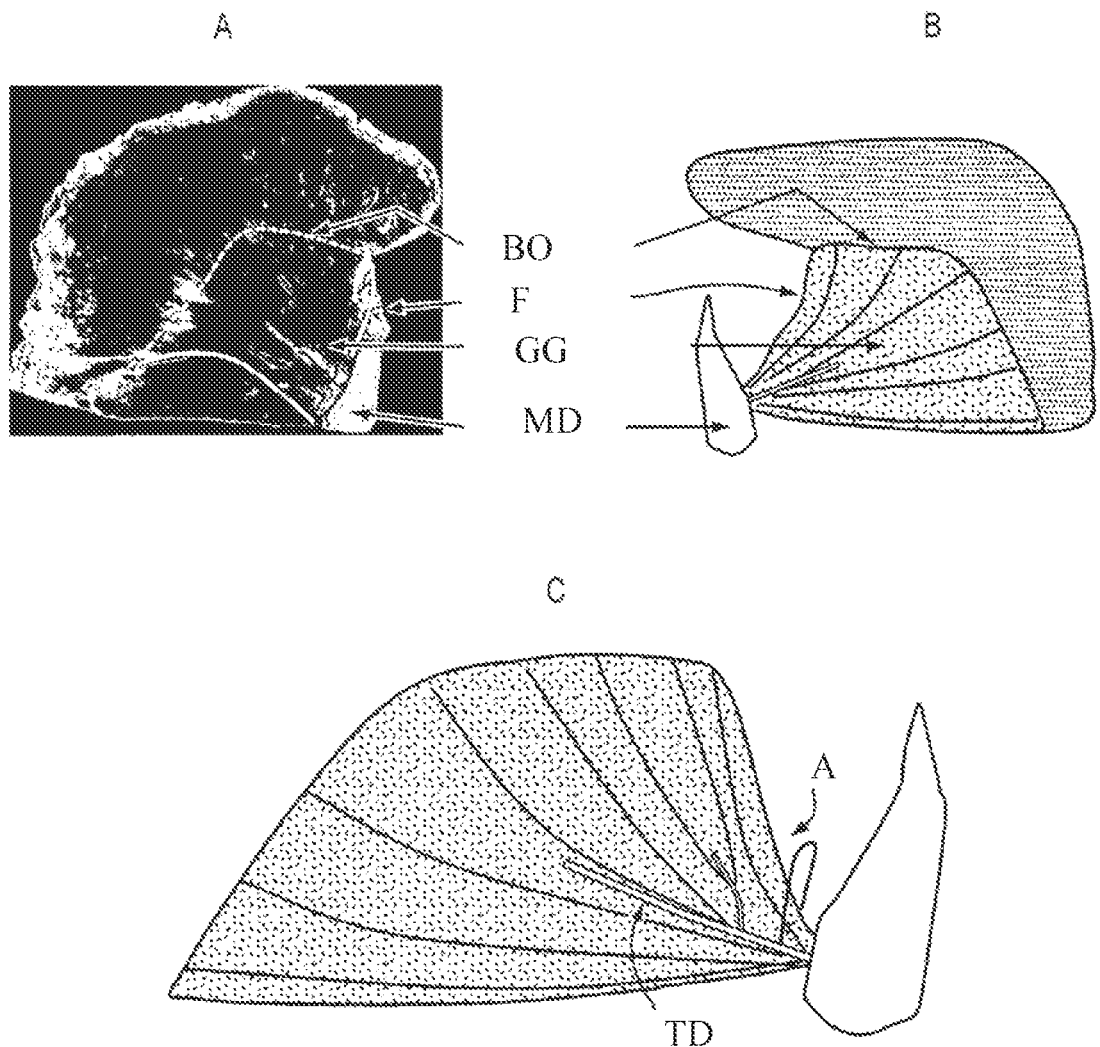
FIGS. 10A-10C illustrate an Anchor member, frenulum area.

FIG. 10. Anchor Member, Frenulum Area.

Within the genioglossus muscle are small tendons upon which muscle fibers insert at various angles. The main tendon is in the middle of the muscle and smaller tendons branch off at various points. Preferably an anchor in the frenulum area (F) is inserted such that its implanted part passes through a tendon (TD). However the anchor (A) can be inserted at any spot in the frenulum area or soft tissue attached to the mandible. The anchor could be coupled to an LTR by a variety of mechanisms as described herein.

A. Side view of the tongue and mandible cut in the centerline (mid-sagittal plane).
B. Drawing of A.
C. Close up of the frenulum area.

Figure 11:
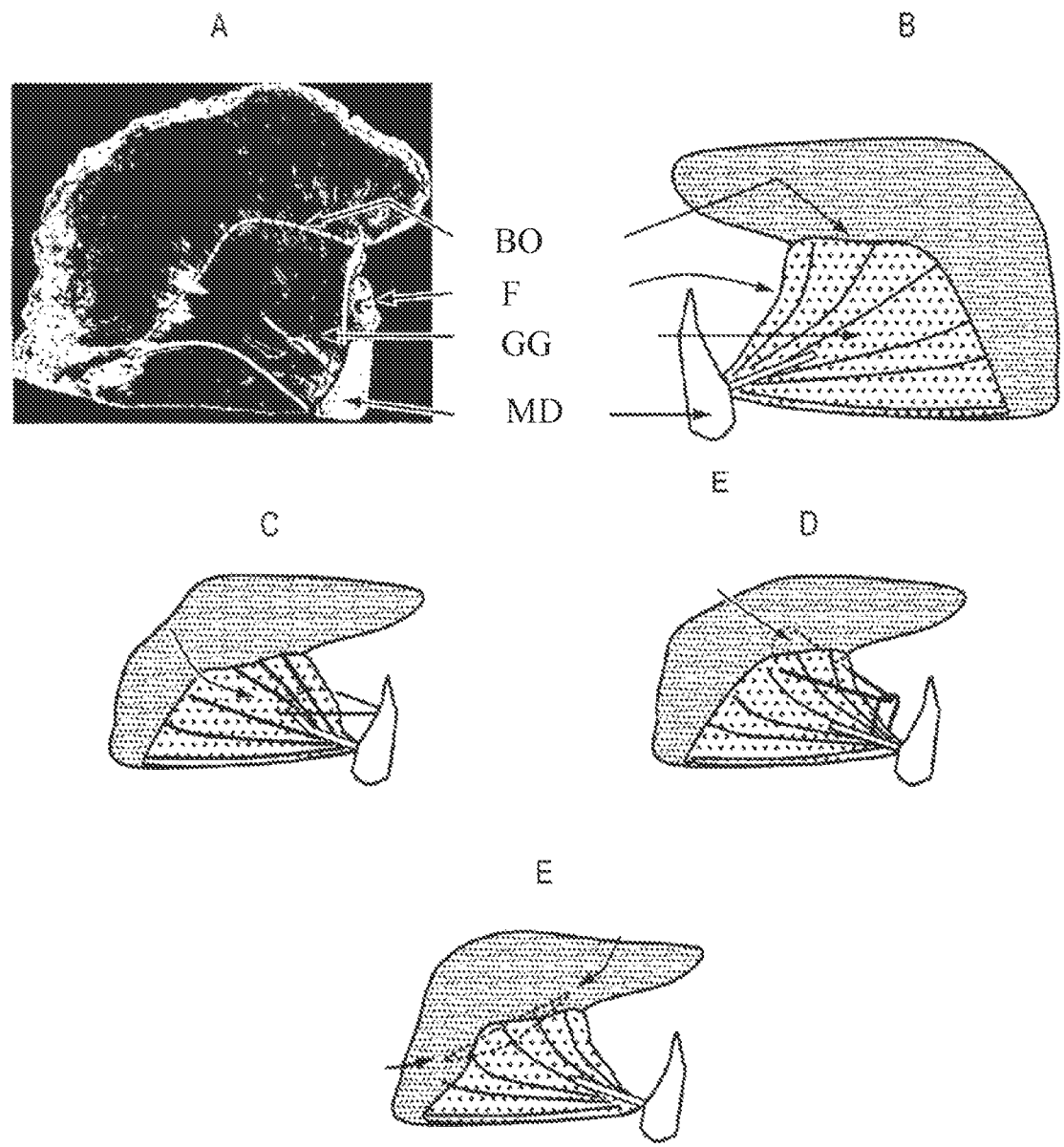
FIGS. 11A-11E illustrate a Frenulum area embodiment.

FIG. 11. Frenulum Area Embodiment.

A. Side view of tongue and mandible cut at the centerline. The frenulum is the front edge of the genioglossus muscle, frenulum area refers to the entire genioglossus and surrounding mucosa. The front and rear boundaries of the genioglossus muscle are marked by solid lines. The genioglossus muscle attaches to a small area on the inner surface of the mandible and tendinous extensions from that area. It fans out from these attachments to insert mostly into connective tissue along the length of the body and base of the tongue called the boundary layer.

B. Drawing of A.

C. Shown is an LTR passing through the frenulum area and anchored externally to a dental anchor. The implanted part of the LTR exerts side forces on the genioglossus muscle fascicles and this is conveyed to the boundary layer and finally to the tongue base (arrow).

D. Shown is an LTR passing through the boundary layer and anchored to a frenulum anchor. Displacement of the tongue is marked by the arrow.

E. Shown is a fully implanted LTR in the frenulum area connecting the boundary area in two places. Note that the beneficial retraction of the tongue base causes some retraction of the tongue blade, however, this does not interfere with tongue function.

Figure 12:
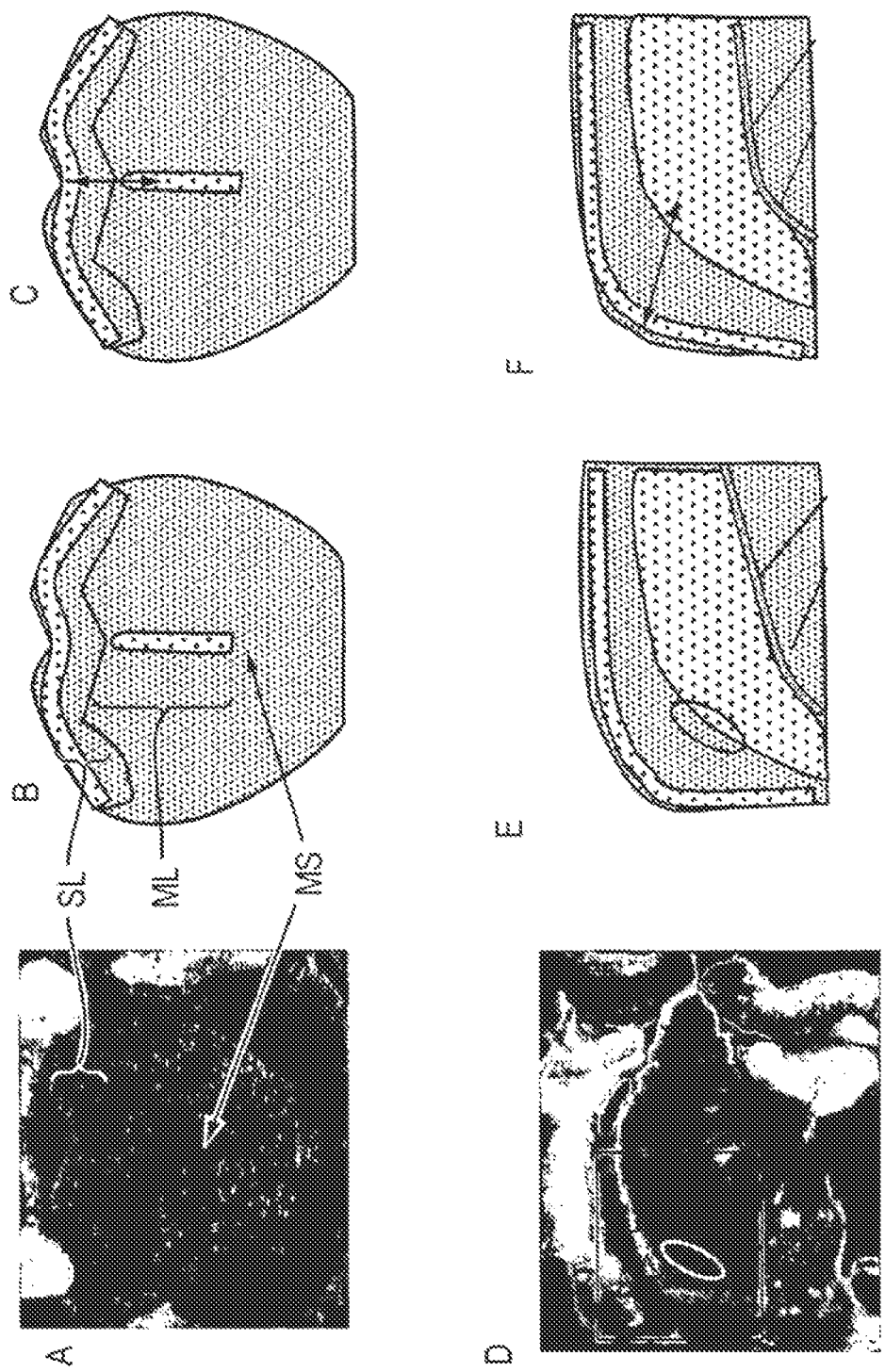
FIGS. 12A-12F illustrate a Tongue base implant.

FIG. 12. Tongue Base Implant.
A. Frontal section of tongue base.
B. Drawing of A. Light lines are the connective tissue of the tongue superior layer (SL) and midline septum (MS). ML, middle layer.
C. Position of LTR implant connecting SL and ML.
D. Tongue seen in mid-sagittal plane. Oval marks the area of mechanical decoupling.
E. Schematic drawing of the box marked in D.
F. Position of implant.

Figure 13:
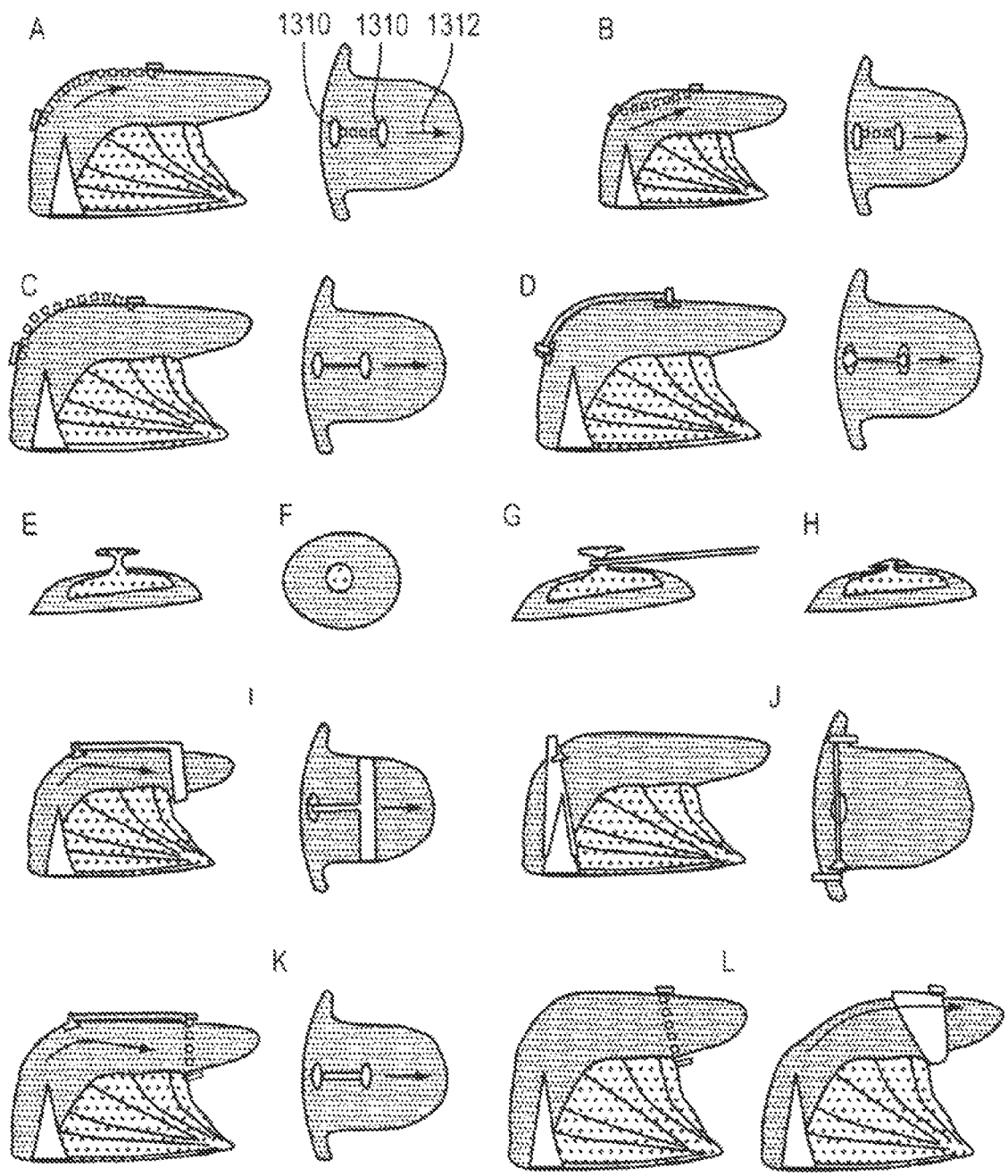
FIGS. 13A-13L illustrate Tongue base embodiments.

FIG. 13. Tongue Base Embodiments
A. Lateral (left) and top (right) drawings of the tongue with an LTR connected by a shaft passing underneath the tongue base mucosa. Green ovals 1310 correspond to anchors and retractors, shaft is dotted yellow when implanted and solid when outside, black arrows 1312 show direction of traction.
B. An LTR with the shaft taking a more direct route between retractor and anchor.
C. An LTR with the shaft exiting from mucosa close to the retractor and anchor.
D. Implanted anchor and retractor with a reversible attachable shaft.
E. Lateral view of a partially implantable anchor or retractor.
F. Top view of a partially implantable anchor or retractor.
G. Partially implantable anchor/retractor showing the shaft connection.
H. Lateral view of a partially implantable anchor/retractor with the extension depressed flush with mucosa when not in use.

I. An LTR with an elastic sleeve placed over the tongue blade and a shaft connecting to a semi-implanted retractor member.

J. An LTR anchored at the PGFs and a shaft passing across the tongue base and connecting to a semi-implanted retractor member.

K. An LTR anchored beneath the tongue blade with a shaft passing through the tongue blade to an intermediate anchor on the superior surface of the tongue. The shaft then passes posteriorly to a semi-implanted retractor member. This allows adjustment of tension from the anchor site beneath the tongue blade.

L. Left, a rigid shaft connects an anchor member below the tongue blade to a retractor member above the tongue blade. The retractor member is rotated forward by a sleeve that is reversibly placed over the tongue blade. The rotation of the retractor member, along with the rigid shaft, displaces the tissue of the tongue base along the midline. Drawing is intentionally exaggerated to show the effects.

Figure 14:
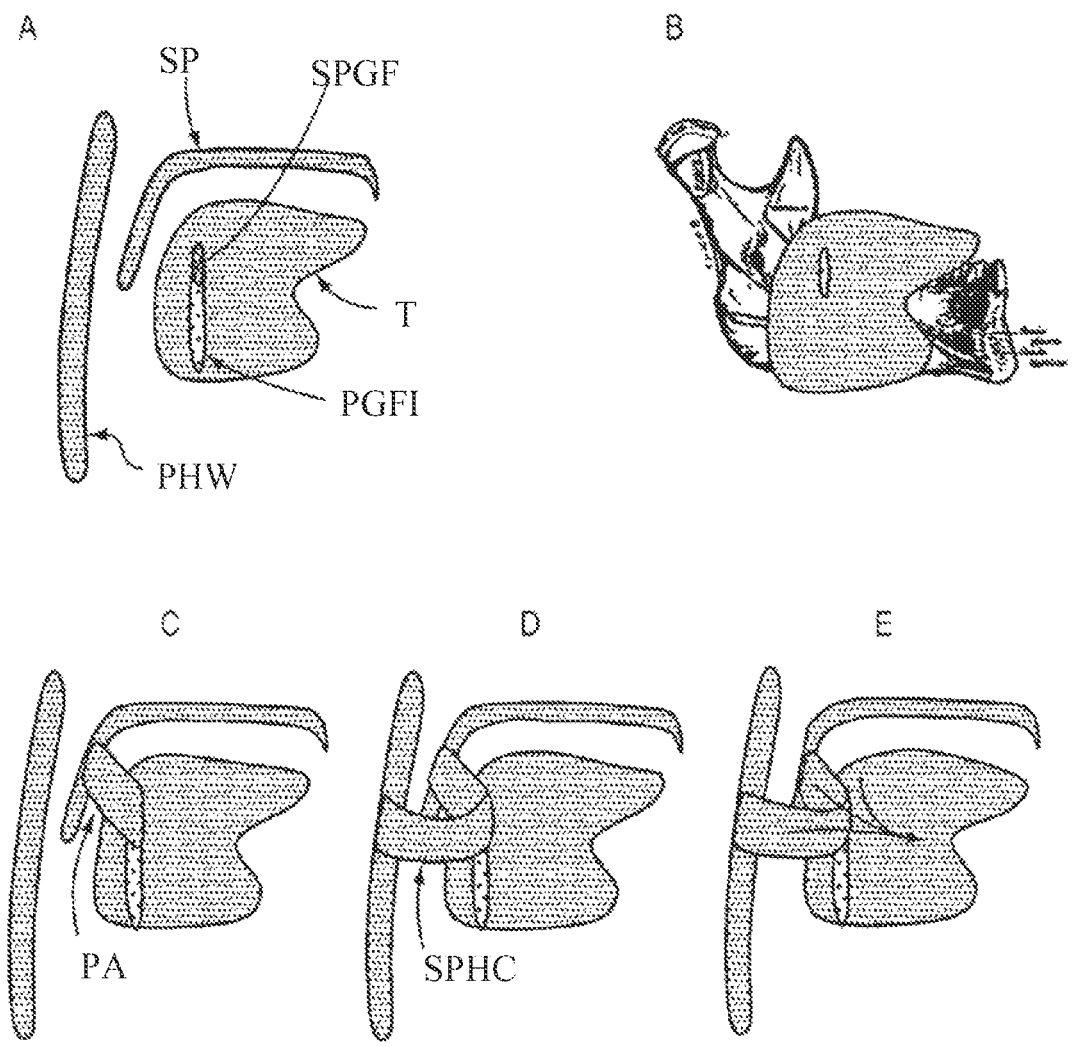
FIGS. 14A-14E illustrate The Superior Palatoglossal Fold.

FIG. 14. The Superior Palatoglossal Fold (SPGF).

A. Side view of the upper airway showing the area of the tongue (T) where the PGF inserts, i.e., the location of the pharyngolassal fold insertion (PGFI). A smaller superior region is of particular significance as it receives overlapping insertions of muscles connecting to the soft palate (SP) and lateral pharyngeal walls (PHW), including but not limited to the palatoglossus (PA) and superior pharyngeal constrictor (SPHC) muscles.

B. Side view of tongue in relation to mandible with the area of superior PGF attachment marked.

C. The palatoglossus muscle is shown connecting the soft palate to the superior PGF.

D. The superior pharyngeal constrictor muscle connects the pharyngeal walls to the superior PGF.

E. Schematic showing that retraction force of the PGF is dispersed to the tongue base, soft palate, and lateral pharyngeal walls.

Figure 15:
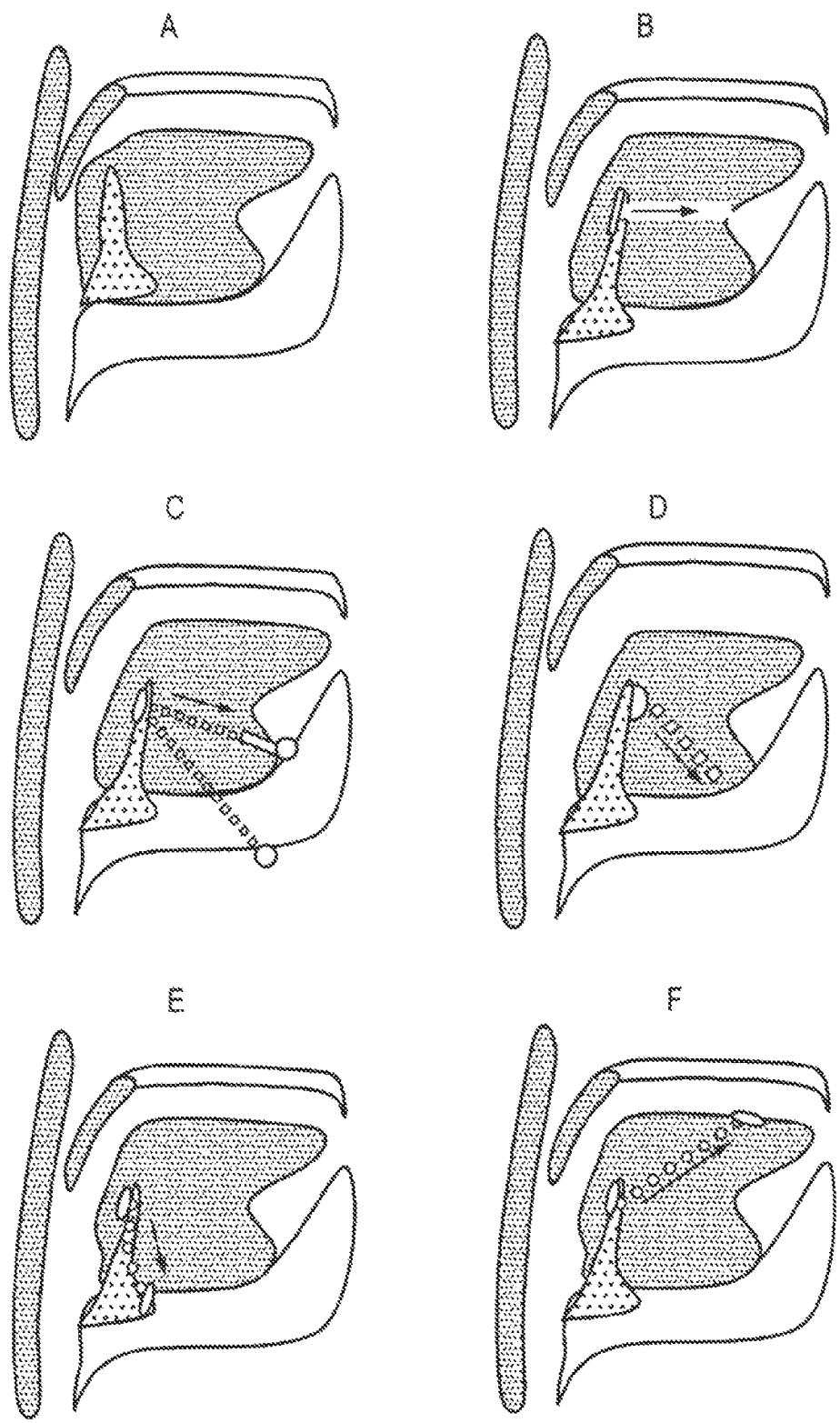
FIGS. 15A-15F illustrate Pharyngoglossal Fold embodiments.

FIG. 15. Pharyngoglossal Fold Embodiments

A. Drawing showing the posterior collapse of the tongue and its effects on the airway.

B. A retractor at the PGF and a shaft that passes across the frenulum to a retractor in the other PGF.

C. A retractor in the PGF and a shaft passing through tongue tissue to emerge and connect to a modified anchor. An alternative embodiment passes through the floor of mouth to an external anchor resting on the skin.

D. An implanted LTR with a retractor in or near the PGF and a shaft passing through tongue to an anchor implanted in genioglossus muscle, or floor of mouth structures.

E. An LTR with a retractor in the superior PGF and an anchor in the inferior PGF.

F. A retractor in the PGF and a shaft passing through tongue to an anchor on the superior surface of the tongue.

Figure 16:
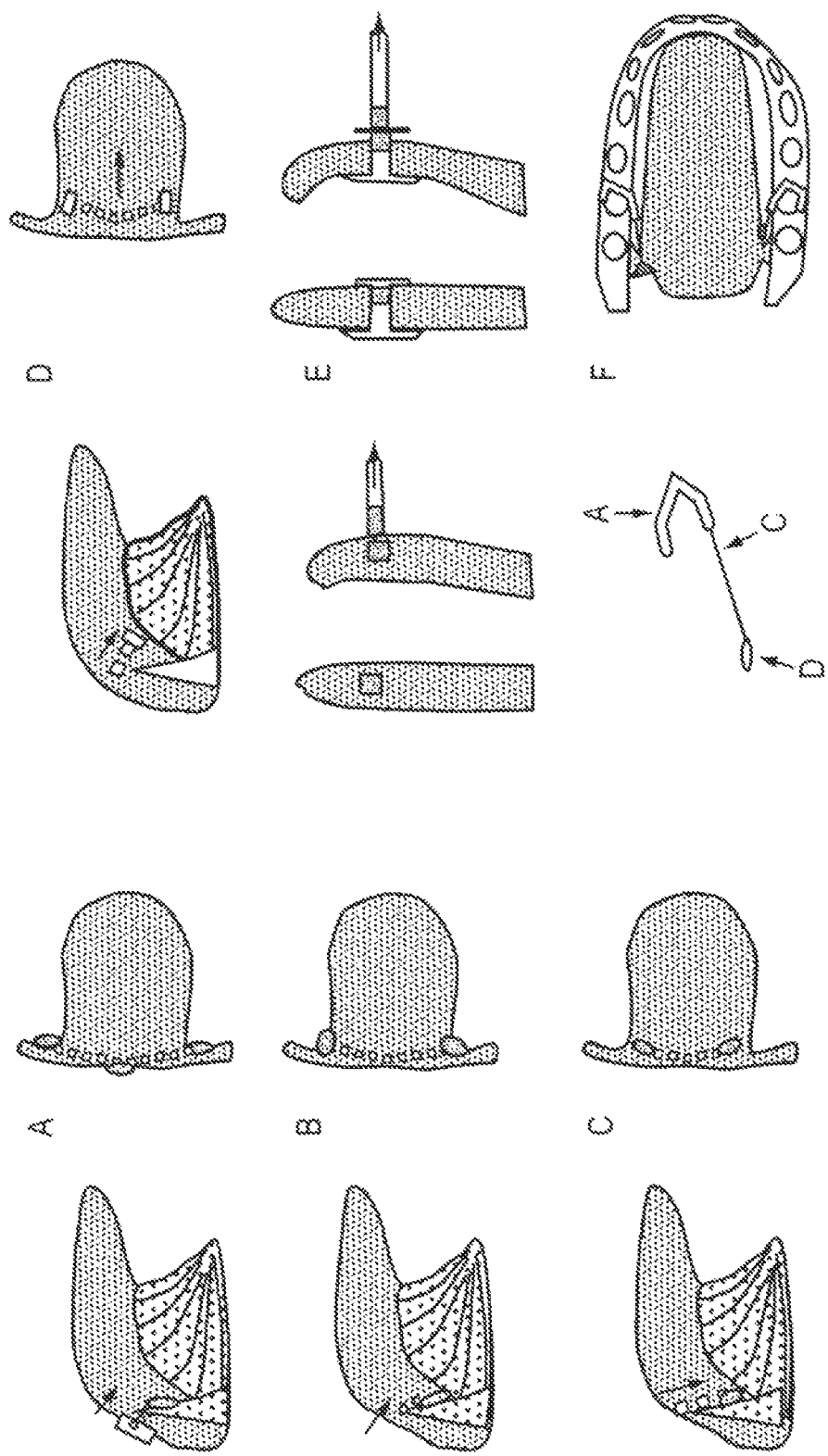
FIGS. 16A-16F illustrate Pharyngoglossal Fold embodiments.

FIG. 16. Pharyngoglossal Fold Embodiments.

A. Retractor at tongue base connected by two sub-mucosal shafts to anchors in front of each PGF.

B. A sub-mucosal shaft connect two retractor/anchor members in front of each PGF.

C. Two implanted retractor/anchor members in or near the PGFs are connected by a sub-mucosal shaft.

D. Magnets implanted in or near each PGF are connected by a sub-mucosal shaft.

E. Left, a magnet implanted in a PGF is retracted by a magnet of opposite polarity attached to a modified anchor. Right, a magnet is enclosed in an implant that has two flanges to keep in place within the PGF.

F. Left, a schematic of a dental type modified anchor. The anchor member is a clasp that reversibly attaches to teeth as shown on right. A shaft of variable length attaches to a retractor member or a coupling mechanism that in turn connects to an implanted LTR. The retractor member may be a magnet or mechanical mechanism. Right, Drawing of tongue and mandible seen from above, Two embodiments of the dental modified anchor are shown: bottom, the retractor member is a magnet that couples to an implanted magnet as shown in E left; top, the shaft ends with a magnet that couples to a reversible magnetic implant as shown in E, right.

Figure 17:
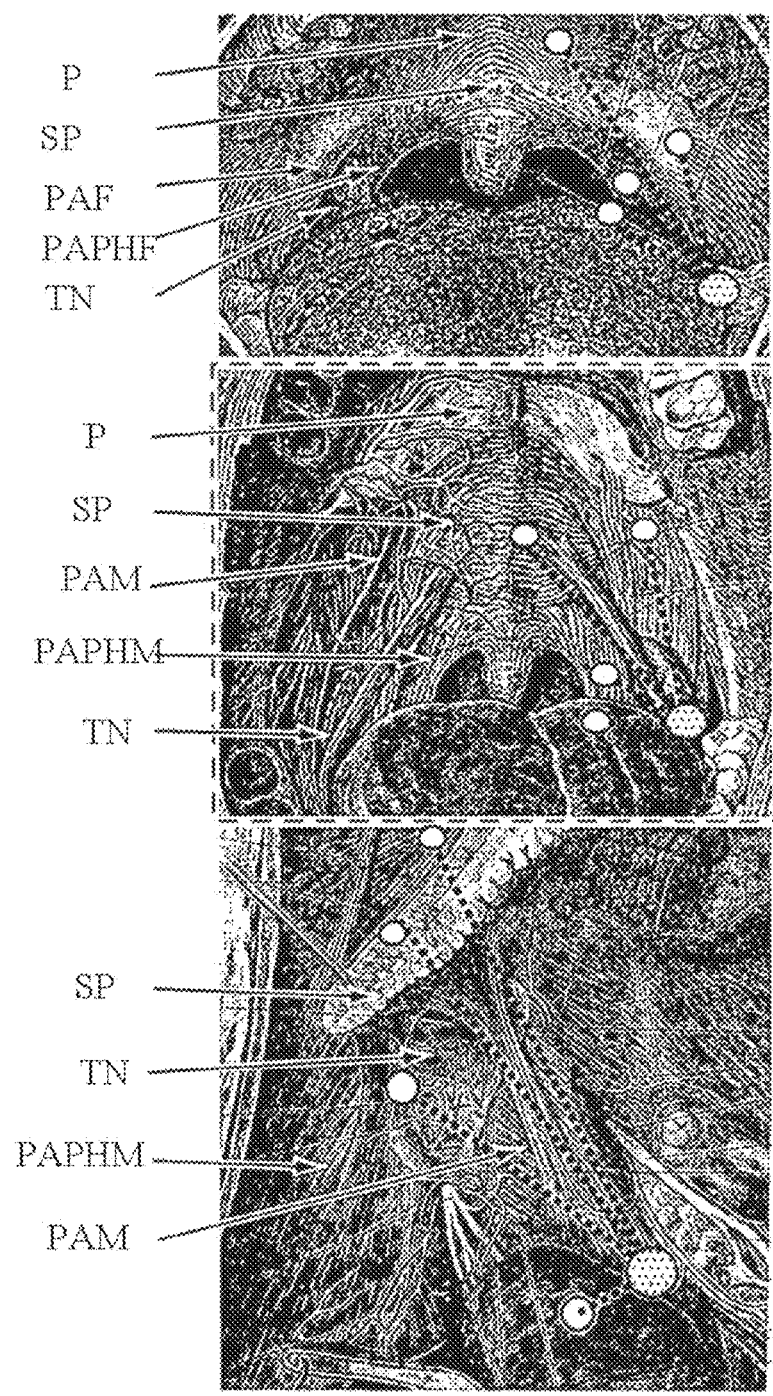
FIGS. 17A-17C illustrate Soft Palate embodiments.

FIG. 17. Soft Palate Embodiments.

A. View of the mouth showing the soft palate (SP), the palatopharyngeus fold (PAPHF) and palatoglossal folds (PAF) (Henry Gray. Anatomy of the Human Body. 1918).

B) Same view as A but with mucosa removed showing the underlying muscles (right side) and the nerve and blood supply (left side).

C) View of the left lateral pharyngeal wall area after mid-sagittal section. Tongue is retracted inferiorly.

Four preferred LTR placements are shown with an anchor in the superior PGF: 1) Shaft passes next to palatoglossus muscle (PAM) around tonsil (TN), retractor rests against lateral edge of soft palate. Preferred embodiment for increasing lateral velopharyngeal area. 2) Shaft travels within palatoglossus muscle, retractor near midline soft palate. Preferred embodiment for increasing medial velopharyngeal airspace; 3) Shaft passes through palatoglossus muscle, palatine tonsil, and palatopharyngeus muscle (PAPHM), retractor rests against posterior wall of soft palate. Preferred embodiment for compression and permanent remodeling of palatine tonsil. 4) Shaft passes 1 cm under tongue base mucosa, retractor rests against tongue base. Preferred embodiment for tensing tongue base.

Figure 18:
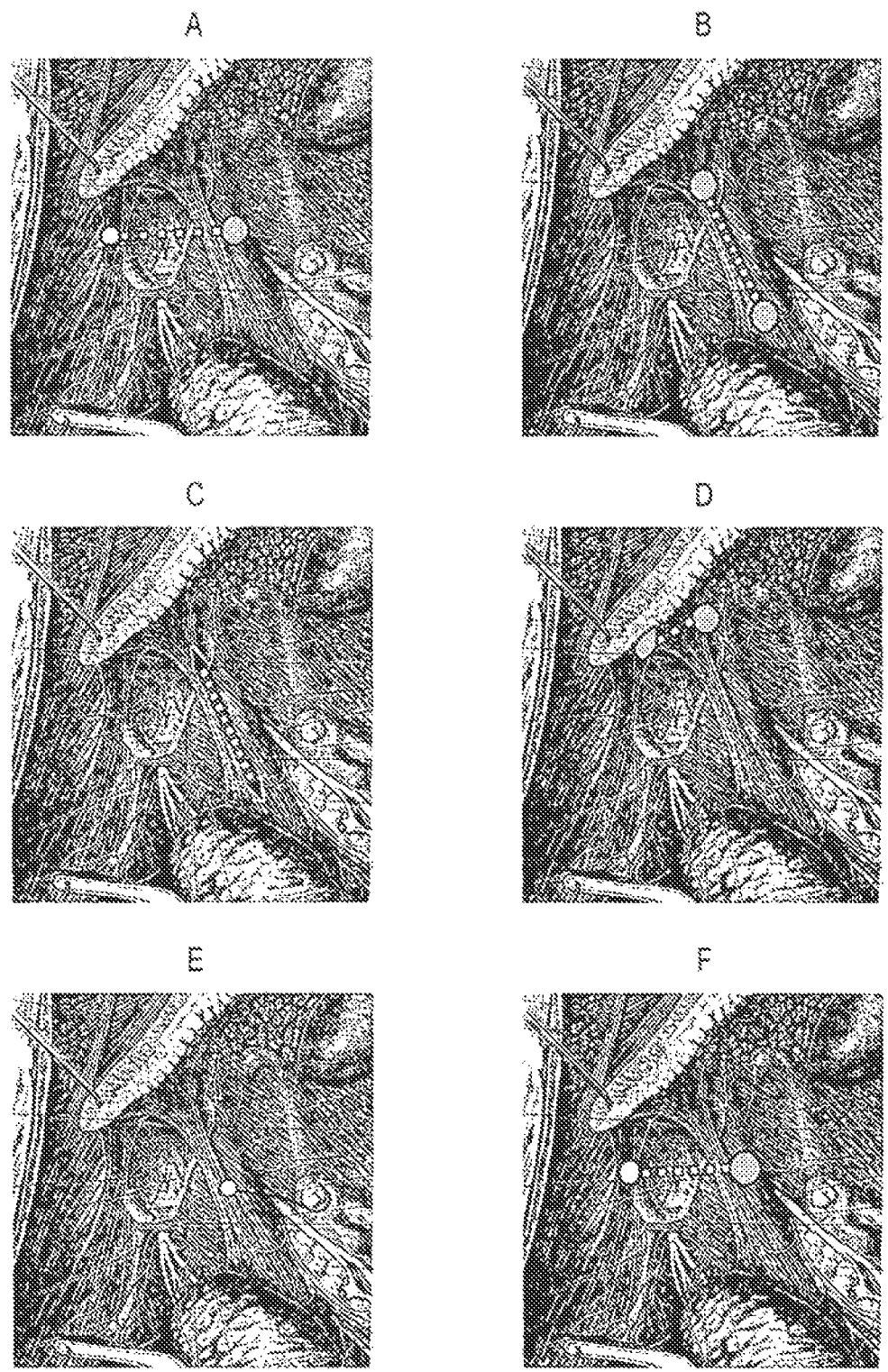
FIGS. 18A-18F illustrate Tonsillar Fold embodiments.

FIG. 18. Tonsillar Fold Embodiments

18A. Retractor posterior surface of posterior tonsillar fold, anchor anterior surface of anterior tonsillar fold. Preferred embodiment for compression of palatine tonsil.

18B. Retractor superior Palatoglossus fold, retractor inferior Palatoglossus Fold or PGF.

18C. Implanted LTR within palatoglossus muscle.

18D. Anchor at lateral aspect of soft palate, retractor midline.

18E. Retractor on inner surface of palatoglossal fold, modified dental anchor.

18F. Retractor at posterior tonsillar fold and anchor at anterior tonsillar fold.

Figure 19:
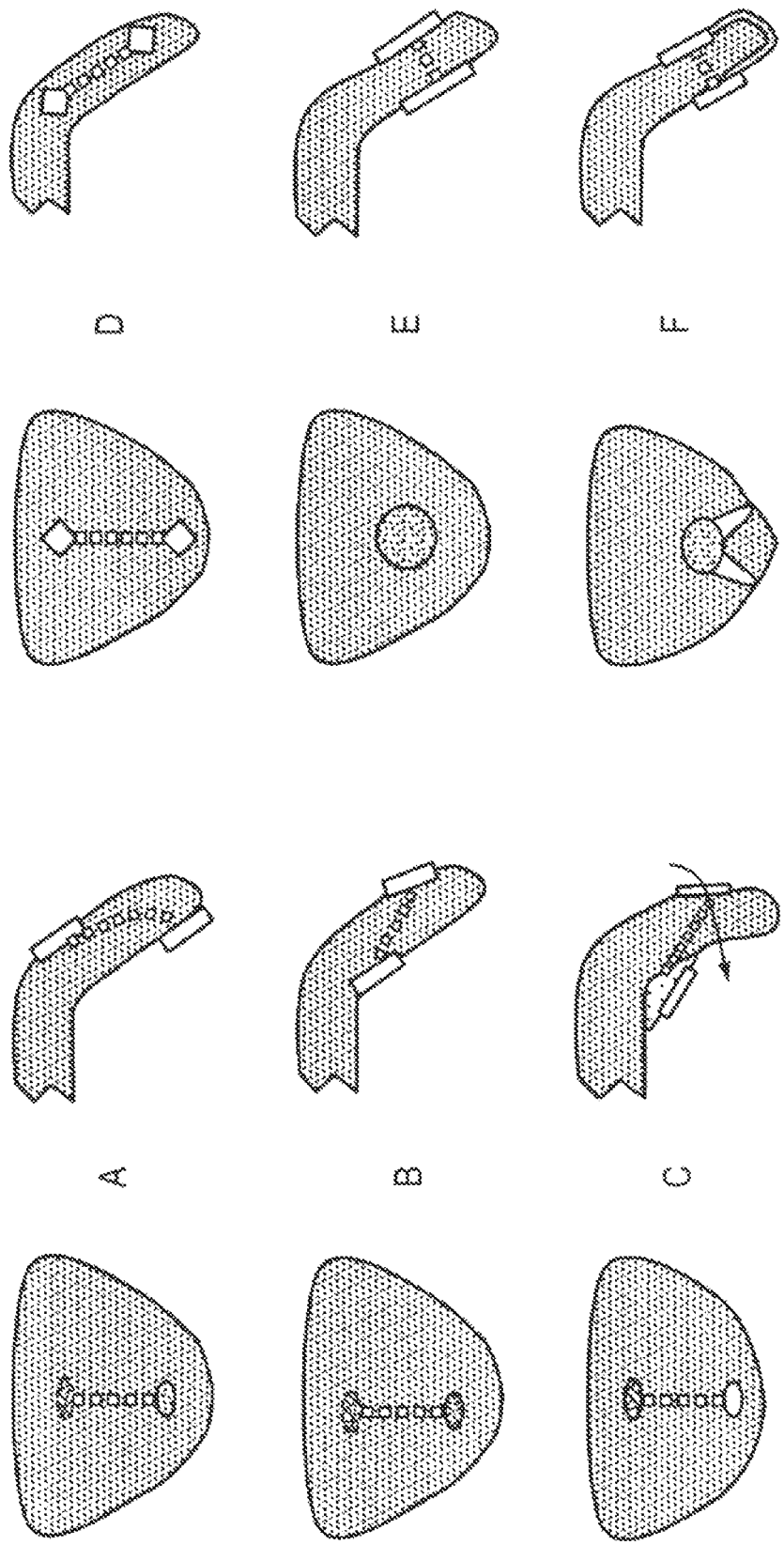
FIGS. 19A-19F illustrate Soft palate embodiments.

FIG. 19. Soft Palate Embodiments

A. Anchor superior pharyngeal side, retractor inferior oral side.

B. Retractor superior oral side, anchor inferior pharyngeal side.

C. Bolster added in front of anchor to load the LTR. Note indentation and rotation.

D. Totally implanted LTR.

E. Opposing retractor and anchor.

F. LTR as attachment for retainers that lift edge of soft palate.

Figure 20:
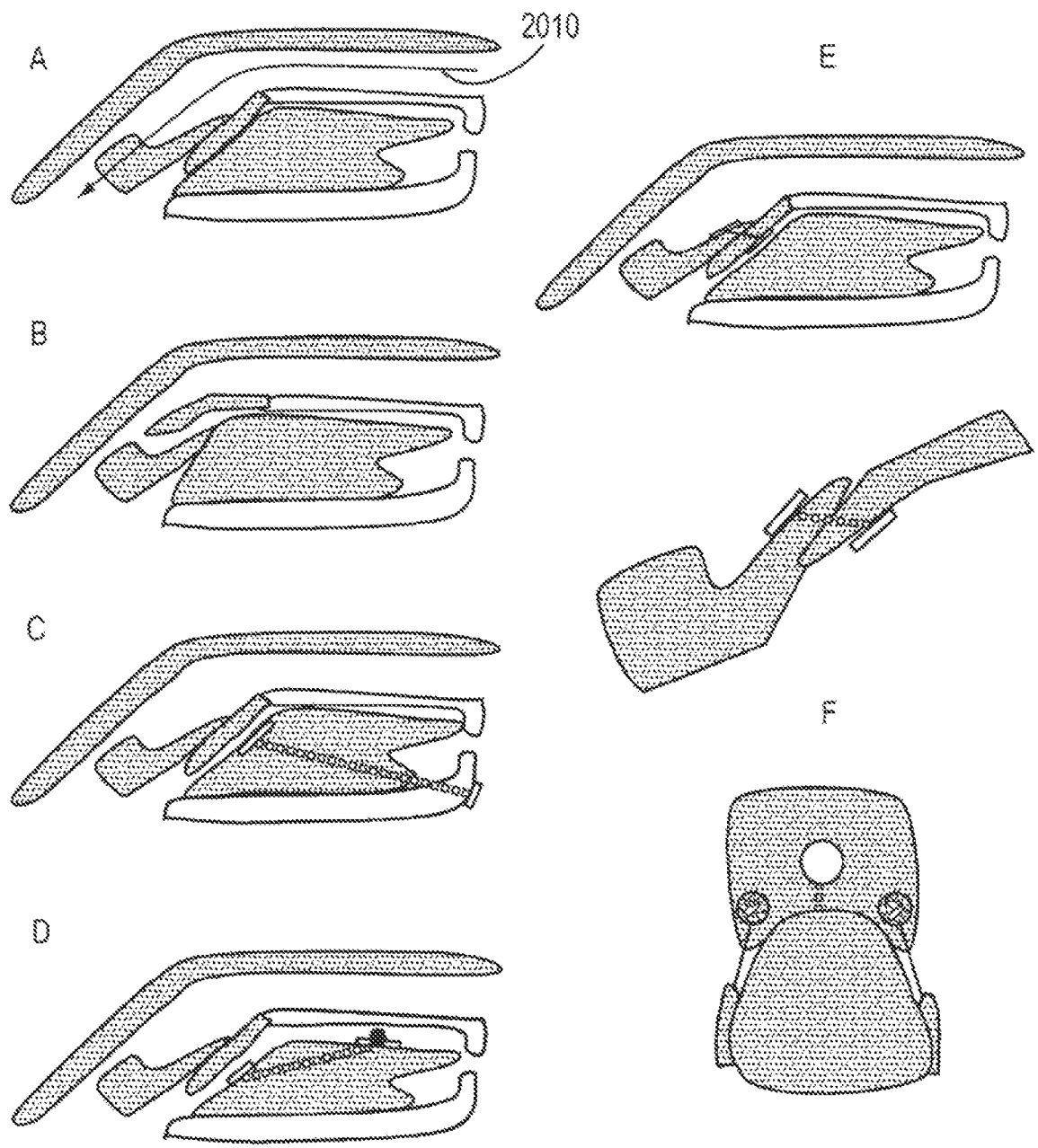
FIGS. 20A-20F illustrate Veterinarian embodiments.

FIG. 20. Veterinarian Embodiments

Shown are embodiments of this invention for equine dorsal displacement of the soft palate.

A. Normal configuration of the horse upper airway during exercise. Note that the soft palate overlaps and interlocks the epiglottis of the larynx to provide an open conduit for airflow (blue line 2010).

B. In DDSP the soft palate is dislodged from its locked position and obstructs the airway. This is believed to be caused by the backward movement of the tongue base.

C. An embodiment of an LTR for this condition. The shaft reaches through the mandible to an adjustable anchor in front of the mandible.

D. Another embodiment where the shaft connects to an anchor on the tongue surface which is reversibly attached to the bit of a bridle during exercise.

E. An embodiment that directly opposes dislodging the soft palate from its normal position. An anchor in front of the soft palate passes backward and then through the epiglottis to a retractor on the laryngeal surface of the epiglottis.

F. In an alternative embodiment an LTR passes from the PGFs to the lateral aspect of the soft palate. View is from the front, tongue is transparent. For comparison the midline embodiment described in E is also shown.

Figure 21:
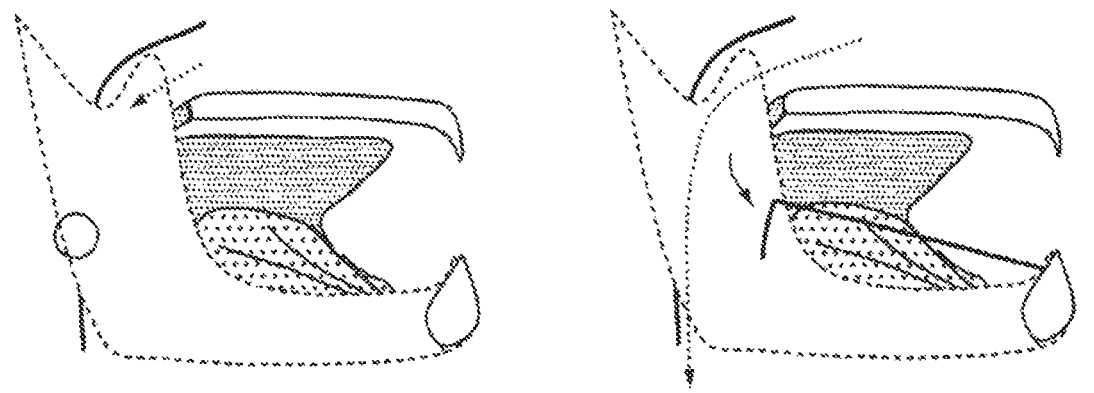
FIGS. 21A-21H illustrate a Non-invasive PGF retractor.
Figure 21:
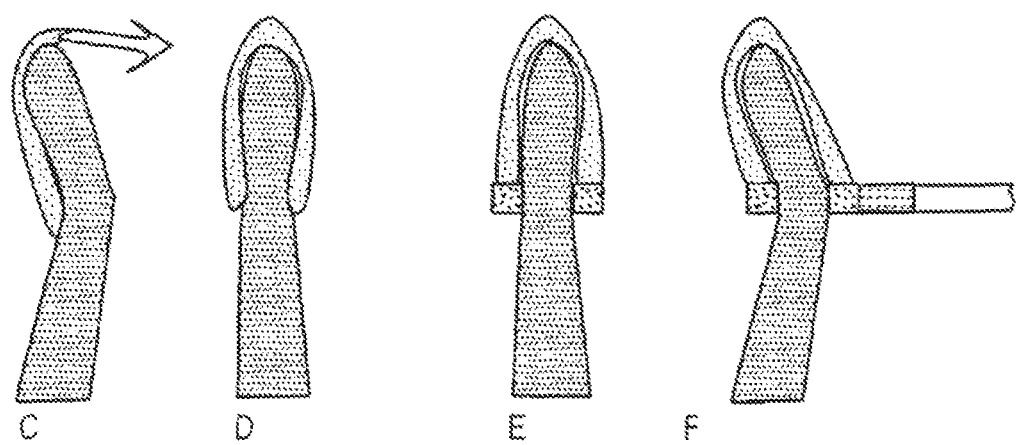
Figure 21:
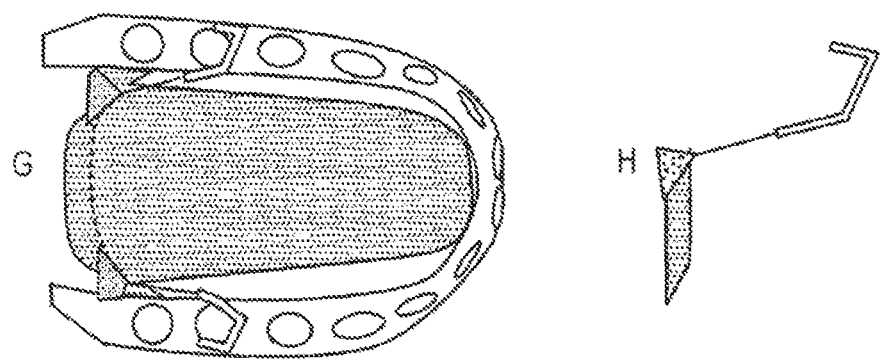

FIG. 21. Non-Invasive PGF Retractor

A. Schematic of airway obstruction due to backward collapse of the tongue.

B. PGF retraction. Soft "hook" retract the PGF forward and thereby retracts the base of tongue, soft palate and pharyngeal walls.

C. Close up view of "hook".

D. Close up view of "clip". Clip remains in place by compressing soft tissue by its arms.

E. An embodiment of the clip where compression is performed by magnets.

F. Embodiment from E where the magnets are also used to couple the retractor to an modified anchor.

G. Drawing of two hook retractors in place and their effect on the tongue base (dotted line).

H. Close-Up View of Hook LTR.

Figure 22:
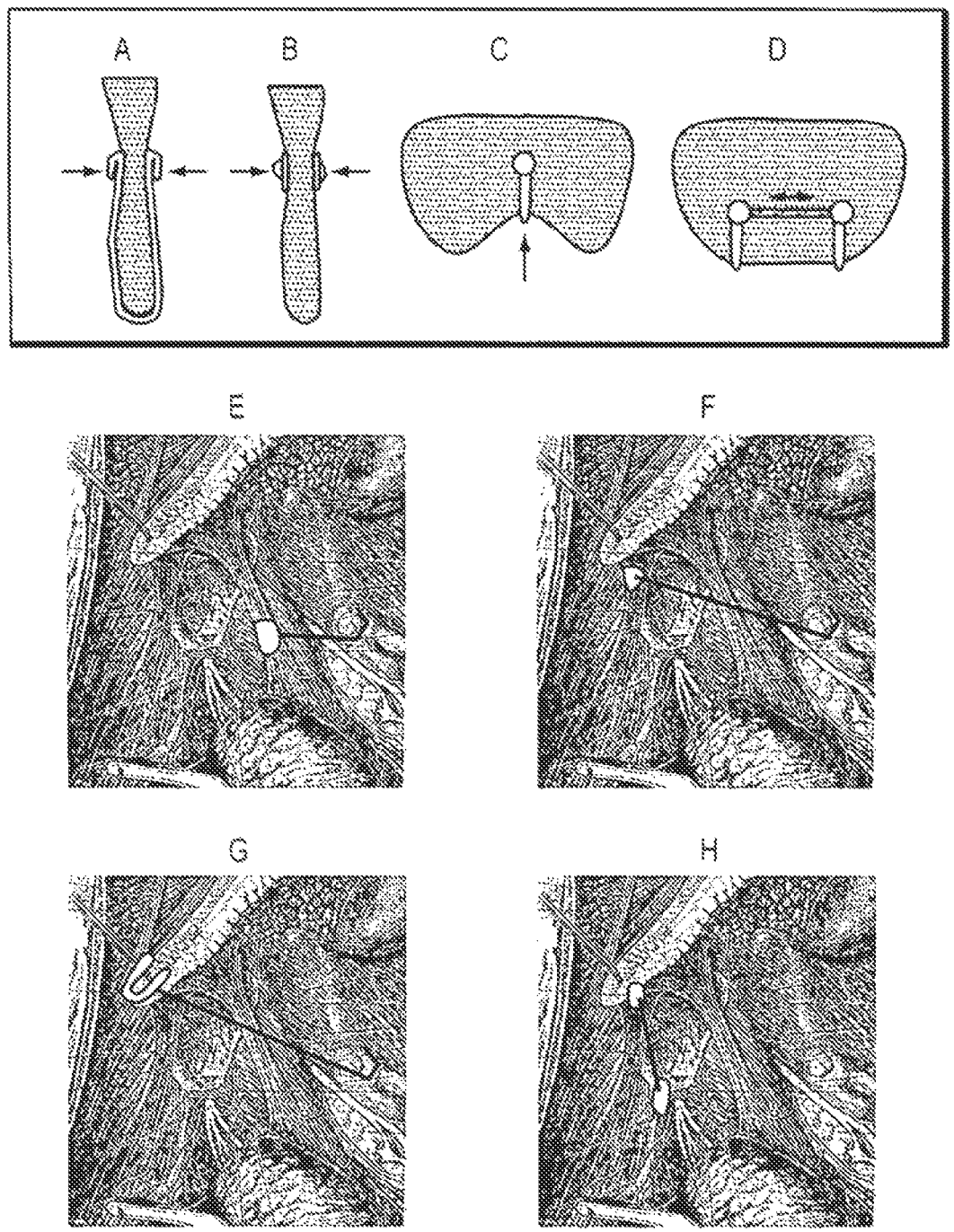
FIGS. 22A-22H illustrate a Non-invasive retraction, clip embodiment.

FIG. 22. Non-invasive retraction, clip embodiment.

A. Side view of clip on soft tissue fold. One method of adhering to the fold is to compress the tissue at the ends of the clip.

B. Side view of clip composed of opposing magnets of opposite polarity. Their magnet attraction provides sufficient force for a stable position and a shaft is unnecessary.

C. Front view of clip on a soft tissue fold. The shaft connection can serve to retract the edge of the fold.

D. Clips used to provide protraction (lengthening, a useful effect on structures that benefit from stiffening such as the soft palate and tongue base.

E. Clip on anterior tonsillar pillar attached to a dental anchor.

F. Clip on posterior tonsillar pillar attached to a dental anchor.

G. Clip on edge of soft palate attached to a dental anchor.

H. Two clips retracting the pharyngeal wall toward the aryepiglottic fold, thus stiffening the lateral pharyngeal wall.

Figure 23:
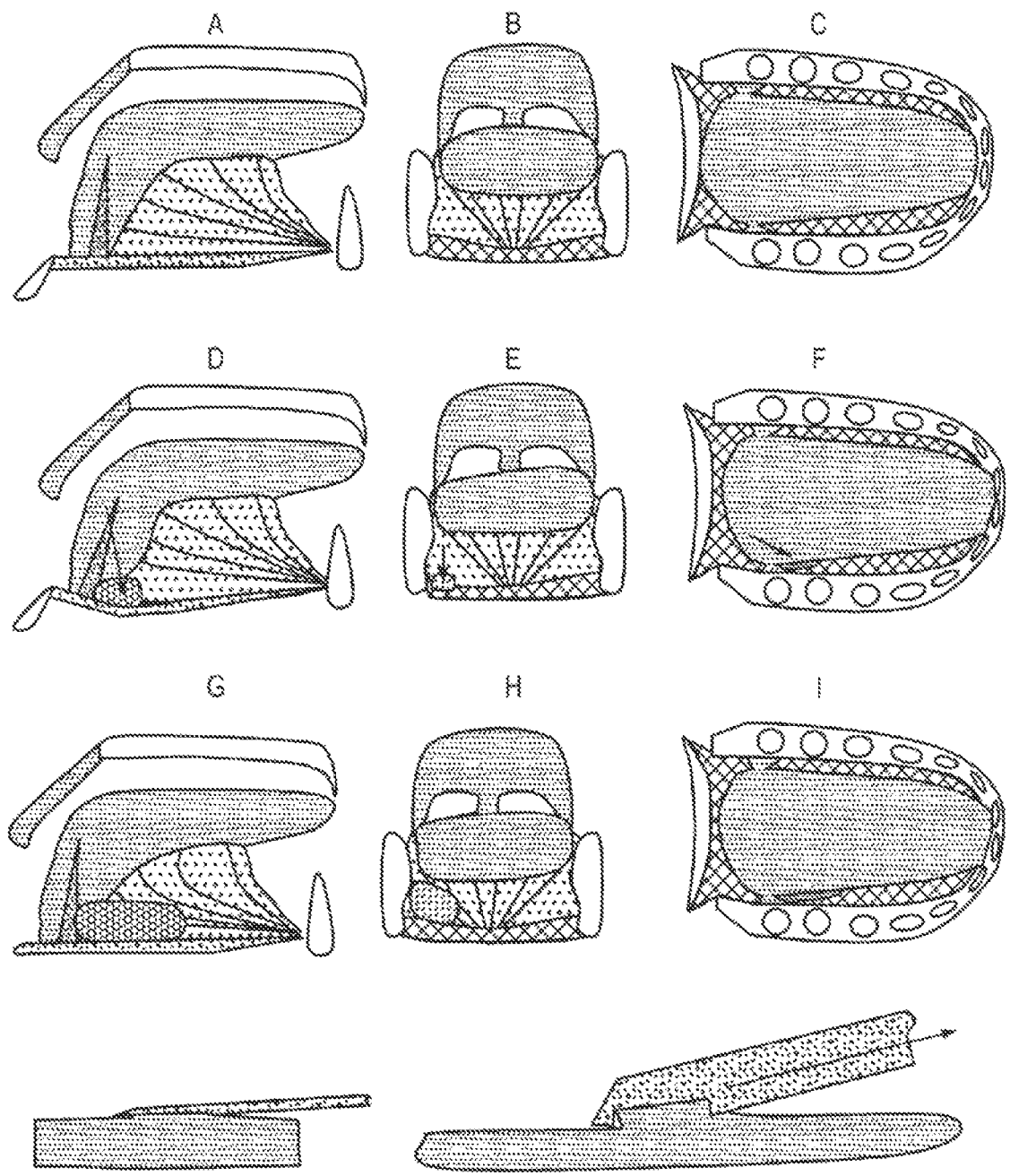
FIGS. 23A-23H illustrate a Non-invasive protraction and vacuum.

FIG. 23. Non-Invasive Protraction and Vacuum. Floor of Mouth Depression.

A. Side view. Floor of mouth is marked by a checkered pattern that extends from the mandible to the hyoid bone.

B. Front view. Floor of mouth connects to the bottom of each side of the mandible.

C. Top view. Tongue is transparent and triangular root of tongue can be seen. The anterior extension of the root is the genioglossus muscle insertion into the mandible.

D. Bolster pushed downward and slightly anterior by a protractor from a dental anchor (not shown). Note the indentation of the FOM and the altered position of the tongue and PGF.

E. FOM depression by bolster reflected by decreased height of tongue surface.

F. Bolster seen from above. Note anterior displacement of base of tongue.

G. A vacuum device applied to the lateral tongue.

H. A vacuum device as a retractor member.

DETAILED DESCRIPTION

The term "subject" as used herein includes animals of mammalian origin, including humans. Anatomical terminology used to describe position and orientation as used herein can best be defined by the following description:

When referring to animals, that typically have one end with a head and mouth, with the opposite end often having the anus and tail, the head end is referred to as the cranial end, while the tail end is referred to as the caudal end. Within the head itself, rostral refers to the direction toward the end of the nose, and caudal is used to refer to the tail direction. The surface or side of an animal's body that is normally oriented upwards, away from the pull of gravity, is the dorsal side; the opposite side, typically the one closest to the ground when walking on all legs, swimming or flying, is the ventral side. On the limbs or other appendages, a point closer to the main body is "proximal"; a point farther away is "distal". Three basic reference planes are used in zoological anatomy. A "sagittal" plane divides the body into left and right portions. The "mid-sagittal" plane is in the midline, i.e. it would pass through midline structures such as the spine, and all other sagittal planes are parallel to it. A "coronal" plane divides the body into dorsal and ventral portions. A "transverse" plane divides the body into cranial and caudal portions.

When referring to humans, the body and its parts are always described using the assumption that the body is standing upright. Portions of the body which are closer to the head end are "superior" (corresponding to cranial in animals), while those farther away are "inferior" (corresponding to caudal in animals). Objects near the front of the body are referred to as "anterior" (corresponding to ventral in animals); those near the rear of the body are referred to as "posterior" (corresponding to dorsal in animals). A transverse, axial, or horizontal plane is an X-Y plane, parallel to the ground, which separates the superior/head from the inferior/feet. A coronal or frontal plane is an Y-Z plane, perpendicular to the ground, which separates the anterior from the posterior. A sagittal plane is an X-Z plane, perpendicular to the ground and to the coronal plane, which separates left from right. The mid-sagittal plane is the specific sagittal plane that is exactly in the middle of the body.

Structures near the midline are called medial and those near the sides of animals are called lateral. Therefore, medial structures are closer to the mid-sagittal plane, lateral structures are further from the mid-sagittal plane. Structures in the midline of the body are median. For example, the tip of a human subject's nose is in the median line.

Ipsilateral means on the same side, contralateral means on the other side and bilateral means on both sides. Structures that are close to the center of the body are proximal or central, while ones more distant are distal or peripheral. For example, the hands are at the distal end of the arms, while the shoulders are at the proximal ends.

Definitions

"Anchor" refers to a component of the device that mechanically couples to a site that is immobile relative to the retractor.

"Deformation" refers to an abnormal change in the shape of upper airway soft tissue structures. This deformation can be due to negative pressure acting on relaxed upper airway structures during sleep causing them to narrow the upper airway. Most preferably this soft tissue can be the tongue curve.

"Frenulum" refers to the vertical anterior edge of the genioglossus muscle. The frenulum passes from the floor of the mouth up to the centerline of the underside of the tongue. The frenulum marks the boundary between the tongue blade and tongue body.

"Frenulum area" refers to the genioglossus muscle and its surrounding mucosa.

"Loaded" refers to an LTR that can have its tension adjusted such that it has minimal tension during the day and higher therapeutic levels of tension at night. The loaded configuration corresponds to the higher therapeutic levels.

"Modified anchor" is an additional component that allows attachment of the permanent anchor of the LTR. In some embodiments the modified anchor allows the patient to adjust tension in the LTR, specifically to increase tension at night and release it during the day.

"Palate retractor" refers to a complete device used for the prevention soft palate deformation.

"Permanent anchor" refers to an anchor component of an LTR that remains on the LTR for the duration of the implantation. The permanent anchor prevents the anterior end of the shaft from slipping back into tongue tissue. In certain embodiments the permanent anchor also serves as a part of a connector when a "modified anchor" is used.

"Pharyngeal wall retractor" refers to a complete device for the prevention of pharyngeal wall deformation.

"Protract" means to lengthen or push apart.

"Reverse deformation" refers to a change in soft tissue shape caused by the tissue retractor. In some embodiments reverse deformation refers to restoring a deformed structure to its normal shape. In other embodiments reverse deformation refers to an indentation of soft tissue in a given area due to the action of a tissue retractor.

"Sleep breathing disorders" refers to all breathing disorders occurring during sleep including but not limited to obstructive sleep apnea, obstructive sleep apnea syndrome, upper airway resistance syndrome, and snoring.

"Tongue base" refers to the part of the tongue posterior to the tongue curve. In anatomical terms the line of demarcation of the tongue base is the circumvallate papillae, a grossly visible line of raised taste organs on the superior surface of the tongue.

"Tongue blade" refers to the part of the tongue anterior to the frenulum. It is covered by mucosa on its top, sides and undersurface.

"Tongue body" is the mid part of the tongue located between the tongue blade and tongue base.

"Tongue boundary" or "boundary" is the inferior surface of the tongue body and base. The genioglossus muscle inserts onto a large part of the boundary.

"Tongue curve" refers to the area of the tongue where its superior surface curves from a horizontal orientation (tongue body and blade) to a vertical orientation (tongue base). Preferably tongue curve refers to the soft tissue in this area between the mucosal covering of the tongue and the connective tissue boundary where the genioglossus muscle attaches.

"Tissue retractor" refers to the complete device of embodiments of the invention for the prevention of soft tissue deformation. The device may be used without limitation in the tongue, soft palate, or pharyngeal walls.

"Tongue retractor" refers to a complete device used for the prevention of tongue deformation. Preferentially it comprises a retractor connected to a shaft which in turn is connected to an anchor.

"Laryngeal retractor" refers to a complete device for the prevention of laryngeal soft tissue deformation.

"Retractor" or "retractor head" or "retractor member" refers to a part of the overall tissue retractor. The retractor physically interacts with soft tissue, either directly or indirectly, to prevent it from deforming. In certain embodiments the retractor head is a disc located on the external surface of the tongue, in other embodiments the retractor head is an inflatable balloon, in other embodiments the retractor head may have curved parts that act like hooks, in other embodiments the retractor head may be a flexible wire passing through the tissue. In some embodiments it may be totally implanted within tissue.

"Retractor shaft", "shaft" or "retractor member" refers to that part of the tongue retractor that attaches to the retractor head and serves to connect it to the retractor anchor. In different embodiments the shaft may be rigid or flexible, solid or hollow, one piece or multiple linked pieces.

"Unloaded" refers to an LTR that exerts little or no tension. As used herein this is usually meant as the configuration during the day. In comparison, the LTR is loaded to therapeutic levels at night.

EXAMPLES

1. Retractor Member (FIG. 6)

Disclosed here is a retractor member that is inserted by a needle and automatically deploys to its working shape.

The retractor head prevents the tongue base from deforming. The preferred qualities for a retractor head that rests upon tongue base mucosa are that its depth is minimal so that it is not noticeable to the patient yet its surface area is large enough to provide sufficient counterforce. Integral to its design is the delivery device used to insert the LTR. It is preferable that the entire device be inserted from the anterior tongue with minimal instrumentation used at the back of the tongue. Therefore the retractor head preferably automatically deploys to its working shape after being implanted by a needle inserted from the front of the tongue.

Part of this aspect of the invention includes improvements in the design of the retractor head that allow it to be easily inserted. In certain embodiments this insertion would be by a needle. Therefore one embodiment of this invention is a retractor head that folds within a needle but deploys to its working shape after insertion. Many mechanisms are known that allow a device to be minimized for insertion in the body, non-limiting examples include nitinol wire, high pressure balloons, and spring mechanisms. These mechanisms work well but add complexity and unnecessary expense.

In a preferred embodiment the retractor component is oval shaped (10 mm long, 5 mm wide, 2.5 mm deep) and is molded together with the shaft (1 mm) as a single piece from moderate consistency medical grade silicon (Shore 80 durometer, Nusil, Ca) (FIG. 6A). The retractor is tilted 75° in relation to the shaft. When the device is threaded into a needle (6B) one side of the oval extends out of the needle port and projects at a 15° angle relative to the outside wall of the needle. When the needle is inserted through tissue this extension is pushed flush against the needle wall and causes a minimum increase in the needle's profile (6C). However, immediately after the needle passes through mucosa the retractor reverts to its extended position (6D). In this manner pulling back the needle causes the retractor to catch mucosa and prevents it from being withdrawn along with the needle. After the needle is removed, minor tension on the shaft causes the retractor head to rotate into proper position and lay flush against the mucosa (6E).

The practical advantages of this invention is that the physician can rapidly and easily insert and withdraw the needle and the device automatically settles into its proper position.

2. Shaft Member. (FIG. 7)

Disclosed here is a modified shaft that adapts its length to avoid interfering with normal movements of the tongue base.

The counterforce exerted against the back of the tongue base is preferably present during sleep but not during the awake state. More preferably, the counterforce is present when the tongue is relaxed and vulnerable to posterior collapse, but not during speech and swallowing. During swallowing the tongue base moves rapidly backward about 1 cm to contact the back wall of the pharynx. The tongue base moves similarly during some speech movements, albeit with much less force. It is desirable that these swallowing and speech movements are not impaired.

In one embodiment of the shaft the section within the tongue is distensible, one non-limiting example being a balloon. Compression of the balloon portion of the shaft allows the shaft to lengthen. During swallowing the tongue contracts forcefully around the shaft. This contraction squeezes the balloon and lengthens it, thereby displacing the retractor head superiorly. As the tongue base moves superiorly in the area of the retractor head during swallowing, the compression exerted on the shaft causes the shaft to lengthen proportionally and prevents the retractor head from exerting unneeded counterforce on the tongue base during swallowing. However, the ability to exert the proper amount of counterforce when the tongue is relaxed is maintained. The amount of distensibility is preferably 0.01 to 10 cm, more preferably 1 cm.

This embodiment is a preferred but non-limiting example of the invention. The decrease of counterforce by the retractor head during swallowing and speech can be accomplished by many mechanical and electromechanical mechanisms known. Those skilled in the art can readily appreciate that the invention can have multiple embodiments.

3. Anchor Member: Bolster, Dental, Implanted (FIGS. 8, 9, 10)

Disclosed here are modified anchors that allow reversible loading of an implanted LTR.

The anchor is the anterior component of the LTR that resists displacement of the shaft and retractor head. In a preferred embodiment the LTR is under little or no tension during the day (unloaded state) and is adjusted to exert tension at night (loaded state). In this embodiment the anchor merely prevents the anterior end of the shaft from being pulled back into tongue tissue. For this purpose a small flange is sufficient. However, at night when further retractor counterforce is desired, the anchor can be replaced, modified, or supplemented; collectively referred to as a modified anchor.

One embodiment of a modified anchor may include a adjustment member, for example, a bolster that is interposed between the permanent anchor and the tongue (FIGS. 8A-8H), such that, after implantation, the retractor, the permanent anchor, and the bolster are external to the soft tissue and the flexible shaft maintains a tension between the retractor member and the anchor member to impart a force on the soft tissue. This bolster either lengthens the shaft, or if the shaft is set at a fixed length it increases the total volume compressed between the retractor head and shaft. In either case, the addition of the bolster of the modified anchor causes a reversible increase in retractor counterforce, i.e., the bolster adjusts the tension between the retractor member and the anchor member. The removable adjustment member may also change the surface area of the anchor member as shown in FIGS. 8A-8H.

In one embodiment of the modified anchor the bolster is composed of silicon gel shaped as a V (FIGS. 8.A, B, and C). The concave inner surface of the 'V' adapts to the wedge shape of the frenulum, the structure underneath the tongue blade. The intent is to spread the retracting counterforce across a wide surface area. In the center of the anchor bolster is a conduit through which the permanent anchor and shaft is threaded. In one embodiment there is a cleft beginning in the center of the top center edge. This cleft is about the width of the shaft but less than that of the permanent anchor. The patient can reach under the tongue and pull the permanent anchor forward (FIGS. 8.D, E, and F), slip the bolster under the tongue, lay the shaft into the cleft, and release the permanent anchor. The permanent anchor then securely rests against the front surface of the cleft and exerts force. The cleft may be reinforced with a harder grade of silicon or another biocompatible material.

Another embodiment of this invention is to secure the permanent anchor to a modified bolster that is permanently or reversibly attached to the teeth, a dental anchor (FIG. 9). Many devices that attach to teeth are known in the art. A non-limiting example is 2T' shaped; the top cross bar of the T rests against the front surface of the lower incisor teeth. The initial section of the vertical line of the T is thin enough to pass between the front two incisor teeth. This vertical part widens to allow the retractor head to be threaded. The final part of the T narrows again to about the width of the shaft. This mechanism allows the anchor to be easily and reversibly attached to the dental bolster (FIGS. 9.A and B).

Another embodiment is a dental anchor optimized for use on the sides of the mouth rather than the front. This embodiment (FIG. 9.C, D) anchors to a molar or premolar tooth or neighboring structures. This embodiment is advantageous due to the short distance between the LTR and the modified anchor, its position on the lateral aspect of the tongue is unlikely to interfere with normal tongue function, and it is easily accessible for placement, adjustment and removal by patient and physician.

In a further embodiment a dental prosthesis is used as an anchor that couples to LTRs in the soft palate, palatoglossal folds, pharyngoglossal folds, tongue, or other upper airway sites (FIG. 9.E). These prostheses are well known in the dental arts, and provide a wide and stable platform for anchoring embodiments of the LTR. Further embodiments can take advantage of the large size and position of these prostheses. Those skilled in the art can understand that a variety of electrical or mechanical mechanisms could be incorporated within these prosthesis. As a non-limiting example, an electrical motor could be used to control the force applied to coupled LTRs at multiple locations in the upper airway.

Still another embodiment of the modified anchor is partially implanted into the floor of the mouth. In one embodiment of this invention a puncture is made across the frenulum or soft tissue structures of the floor of the mouth. A flexible shaft is threaded through the puncture and the ends connected to make a ring like structure. This modified anchor therefore is securely fixed within tissue while the remainder lies along the floor of the mouth (FIG. 10). The modified anchor then can be reversibly attached to the permanent anchor at night and disengaged in the morning.

4. Frenulum Area Embodiments

Disclosed are methods and devices for retracting or preventing deformation of the tongue base by retracting the genioglossus muscle or the boundary fascia upon which genioglossus muscle inserts (collectively referred to as the frenulum area).

It has been unexpectedly found that the shaft of the LTR can be safely passed across the undersurface of the tongue. This tissue contains the genioglossus muscle and its anterior edge is the frenulum (FIG. 11.A, B). The genioglossus muscle originates from the mandible and has multiple separate muscle fascicles that fan out from a horizontal to vertical angle. The genioglossus fascicles attach to a layer of connective tissue within the tongue called the boundary (FIG. 11.A, dotted line). The genioglossus fascicles normally act by exerting force in the axis of the fascicle onto the part of the boundary to which they are attached. However, even when inactive the fascicles are mechanically coupled to the tongue boundary and can exert force if passively moved. Unexpectedly, this can be done by pulling these fascicles perpendicular to their axis (FIG. 11.C). To simplify the mechanism, the genioglossus fascicles are lassoed by the LTR shaft.

There are certain important considerations in placing a retractor through the genioglossus: First, the genioglossus is soft in comparison to the tongue base, therefore too much force applied in a localized area can tear the tissue or cause undesirable tissue remodeling over time, sometimes called the "cheese cutter effect". However, there is a central tendon to the genioglossus that is very strong. This tendon is located approximately 1 cm from the edge of the frenulum. Second, the nerve supply to the genioglossus passes along the superior aspect of the muscle, therefore the top 0.5 cm of the muscle, the area directly below the tongue blade, is not a preferable site for the implant.

In one embodiment the shaft is a 5 cm length of elastomeric material that is ribbon shaped. The cross sectional dimensions are 0.5 mm depth and 3 mm width. The wider dimension of the ribbon will exert force on the tissue as its force is dispersed over a wider area than the narrow edge of the ribbon. The shaft is attached to a needle and passed through the muscle approximately 1 cm behind the frenulum. The ends of the shaft are then reversibly coupled to a modified anchor. The middle section of the shaft itself exerts anterior retracting force onto the genioglossus muscle and acts as a retracting head: one or both ends of the shaft can then be brought forward and secured to a modified anchor. This displacement is transmitted to the tongue base causing some degree of concavity. The passive movement is preferably in an anterior and inferior direction.

The advantages of genioglossus muscle retraction is that this muscle group is easily accessible beneath the tongue. The tissue is soft and easily compressed, making it easy to pierce without complications. The position under the tongue is invisible to others, a quality important for the patient.

A further embodiment of this invention is to pass the LTR deeper into the tongue to couple directly to the boundary layer (FIG. 11.D). The boundary layer is a relatively firm connective tissue structure which spans the length of the body of the tongue and receives the insertion of the genioglossus muscle. The advantages of coupling to the boundary layer are that it provides a more secure attachment then the genioglossus itself. However, greater care is needed for placement of the device. Specifically the lingual arteries course just superior and lateral to the boundary layer so it is essential that the insertion be made medial to this structure.

In a further embodiment a fully implanted LTR connects one site that effects the tongue base and is anchored at another site that does not. A non-limiting example is shown in FIG. 11E. Here the posterior boundary layer is coupled to the anterior boundary layer. Tension between the two sites displaces the tongue base forward. Simultaneously there is some displacement force exerted around the anterior boundary site but this has insignificant effects on normal tongue function.

5. Implanted Tongue Base Retractor (FIG. 12)

Disclosed here are methods and devices that are implanted within the tongue and exert highly localized forces to prevent mechanical decoupling of tongue base structures.

Chronic implants within the tongue are technically challenging and potentially dangerous. The tongue is a mobile structure and tongue movements during swallowing and speech are dependent on this mobility. The tongue has no bones within it and its mechanism of movement is unique among the muscular structures of the body. Most skeletal muscles are attached to bones and movement occurs as mechanical levers. In the tongue structures cause movement by expanding and changing their shape and volume. The mechanism is called a muscular hydrostat and can be likened to a flexible hydraulic system. In addition the tongue has extensive nerve and blood supply that can be easily damaged. Moreover, the tongue has a tremendous ability to remodel itself when effected by implants and other forces. This is why many prior art devices have failed due to gradual loss of tension or extrusion. Moreover any implant is a potential site for infection and scarring. For these reasons any invasive intervention in the tongue must be designed with a detailed knowledge of tongue anatomy and physiology.

Therefore the implanted embodiments disclosed in this invention are carefully designed to be as minimally invasive as possible and to focus their effects on the most critical areas of pathology without risking interference with normal function.

A preferred embodiment of an implanted LTR disclosed here is a very minimal device implanted into the tongue base.

The tongue is covered by mucosa and this mucosa has underlying connective tissue. The connective tissue is thickest below the superior surface of the tongue. This superior surface is intimately connected to the underlying superior longitudinal muscle. Together the mucosa connective tissue and muscle form a superior layer (SL) that spans the superior surface of the tongue from the tongue tip to its base. This superior layer is normally coupled to the underlying middle layer of the tongue which is largely composed by the transverse muscle. The transverse muscle originates from a fascial sheet called the medial septum (MS) oriented in the centerline of the tongue (mid-saggital plane).

Although not wishing to be bound by theory studies by the inventor suggest that the vibration during snoring and the stretching during airway obstruction gradually loosen the attachment of the superior layer to the middle layer. This is reflected by the widening of the superior layer in the area of the tongue curve, marked by an oval. This mechanical decoupling results in a more flaccid and compliant tongue base that deforms more easily when the pressure in the airway decreases, thereby making the patient susceptible to sleep apnea and other sleep breathing disorders.

In one embodiment of the invention a very small LTR can be inserted at the curve of the tongue base to correct the mechanical decoupling of the tongue layers. The LTR is symmetrical with an arrowhead shaped retractor head and anchor. Each end of the LTR mechanically hooks into soft tissue, preferably the connective tissue fascia of the mucosa and the midline septum. The hooking mechanism can be quite varied as many variations are known in the art. Non-limiting examples are: hooks, barbs, helixes, staples, screws, sutures, biointegrated permanent material, collagen, and elastin. However, the preferred embodiment is as simple as possible: a short elastic shaft with a hook of firmer consistency at either end.

In alternative embodiments the implanted LTR can vary from 1 mm to 3 cm. Longer LTRs can couple the tongue base tissue to the boundary fascia between the tongue and genioglossus muscle, through the boundary layer to the genioglossus muscle, floor of mouth or mandible via barbs, hooks, fibrotic reaction, or other methods known in the art. The implant can be composed of biodegradable material that decomposes in a week to a year. Many materials used for surgical sutures can be adapted for this purpose.

Preferably the shaft is oriented such that the force on the retractor is at least one orientation that includes downward, forward, and to the side. Multiple implants may be used along the midline to distribute the coupling force without interfering with normal function. Depending on the anatomy of the patient implants may be inserted at any site in the tongue however, more preferable is the midline of the tongue and most preferable is the midline of the tongue curve. One or more of the following aspects of the invention can be used to mold the effects for the exact needs of the individual patient: implant site and orientation, shaft length and elasticity, and hook size, shape, and hardness.

Preferably the implant is bioresorbable over a period of 1 day to 10 years, more preferably 1 month to 1 year, most preferably 1 month to 6 months. The most preferable time range allows sufficient time for remodeling of the tongue and persistent if not permanent restoration of mechanical coupling in the area. Permanent implants are less preferable.

It is preferable that permanent or resorbable implants be inserted into superficial levels of the tongue in areas that do not normally undergo a great amount shape change during normal tongue activity. This minimizes the possibility of interference with normal function, particularly if there is an infection or fibrous reaction to the implant. To plan for atraumatic removal of the implant in cases of infection, pain or other complication, the implant should be designed to be easily removed without extensive surgery. To facilitate removal of the implant, the tear strength of the hooking mechanism should preferably range from 1 to 1000 grams. More preferably 10 to 100 grams. Preferably the arms of the hook would fold straight at these tear strength limits, allowing the implant to be removed without further damage to tissue as it is extracted.

6. Tongue Base Retraction (FIG. 13)

Disclosed here is an embodiment of this invention that focuses on retracting tissue of the tongue base, particularly the tongue base mucosa. This has the advantage that it is easy to insert by the physician, minimally invasive and easily adjustable by the patient.

In one embodiment the device is inserted from one site to another on the superior surface of the tongue. The anterior part of the device is the anchor and the posterior part is the retractor. Tension between the two retracts the tongue surface and displaces the tongue base. Although the counter traction affects the anterior tongue surface it has no effect on normal function.

The shaft either passes directly underneath the mucosa (13.A) or takes a more direct line through the tongue (13.B). Passing the shaft directly underneath mucosa is easier for the physician. In this configuration the force at the retractor head is oriented laterally, and this causes the mucosa posterior to the retractor head to be pulled taut with some degree of indentation. In the more direct route the retraction force is oriented close to perpendicular to the tongue surface and there is more indentation then mucosal tension. The exact orientation at insertion can be varied to maximize the beneficial effects for the patient.

In another embodiment the shaft reemerges in close proximity to the anchor and runs most of its course along the surface of the tongue. This has the advantage of avoiding even the minimally invasive tunnels formed by A and B. Furthermore the configurations can be combined and the shaft can travel the entire distance under the mucosa or can re-emerge one or more times (13.C).

In another embodiment the anchor and/or the retractor can be embedded beneath mucosa and the shaft is detachable (13.D). In a preferred embodiment the anchor/retractor would be a silastic disc 5 mm in diameter that is implanted under the mucosa. The disc has a 1 mm diameter extension that comes out of the pocket. The extension ends in a 2 mm disc (13.E, F). This extension reversibly couples to a shaft. Preferable shafts would be elastomeric. One preferable embodiment would be a simple medical grade rubber band. Another embodiment is a 1×1 mm strip of elastomeric material with expansion at either end to accommodate precut keyholes for attachment to the implanted anchor/retractor. These attachment holes would have 2 mm or greater inner holes to allow the stretched shaft to pass over the extension and 1 mm outer holes or clefts that slot into the extension (13.G). Materials could be pigmented to match the color of the tongue mucosa. A further embodiment would allow the patient to depress the elevated extension so that it is flush with the mucosa, particularly when not in use (13.H). Many mechanisms are known in the art to allow reversible depression of a button like device.

A further embodiment is an anchor member composed of an elastic sleeve slipped over the tongue blade (13.I). The shaft may be an integral part of the sleeve or a separate attachable component. The sleeve is preferably composed of silicone or other biocompatible elastomers. The distal end of the shaft can be reversibly attached to the implanted retractor head. The mechanism by which the shaft and implant are coupled may include elastic bands, clips, magnets of opposite polarity, and other mechanisms well known to those skilled in the art. The advantages of this arrangement are that only a small partially embedded implant is needed to achieve retraction.

In a further embodiment two anchors are placed in the PGFs (13.J). The anchors are attachment points for an elastic band passing over the base of tongue that serves to retract the base, or presses upon a smaller retractor component that is semi-implanted.

In a further embodiment an LTR anchored beneath the tongue blade with a shaft passes through the tongue blade to an intermediate anchor on the superior surface of the tongue. The shaft then passes posteriorly to a semi implanted retractor member (13.K). This allows adjustment of tension from the anchor site beneath the tongue blade.

In a further embodiment a rigid shaft connects an anchor member below the tongue blade to a retractor member above the tongue blade. The retractor member is rotated forward by a sleeve that is reversibly placed over the tongue blade. The rotation of the retractor member, along with the rigid shaft, displaces the tissue of the tongue base along the midline (13.L)

7. Pharyngoglossal Fold (PGF)

Disclosed here are methods and devices for using the PGF as a retractor or anchor site in order to beneficially effect the tongue, pharyngeal walls and/or soft palate.

On both sides of the tongue thin folds of mucosa connect the tongue to the mandible. These are called the pharyngoglossal folds (PGF). Within these folds are the palatoglossal, superior constrictor, styloglossus and hyoglossus muscles, from superior to inferior respectively. The PGFs separate the oral cavity (anterior) from the pharynx (posterior). Anterior to this attachment there is no lateral connection of the tongue and it is freely mobile. One of the muscles within the PGF is the palatoglossus which courses superiorly to connect with the soft palate, thereby forming what is seen in the mouth as the anterior tonsillar pillar.

Unexpectedly the PGF has been found to have several advantages as a retraction site that enlarges the pharyngeal airspace. The corrective tissue of the PGF is connected with that of the tongue. Therefore, it has been unexpectedly found that traction on the PGF is transmitted to the base of tongue. Moreover, as the superior pharyngeal constrictor and palatoglossus muscles are attached to the PGF and in turn connect with the lateral pharyngeal walls and soft palate these structures can also be retracted (FIG. 14). In particular a preferred site within PGF is its superior end where many of these muscles overlap as they insert into the tongue. Therefore retraction at one site expands the pharyngeal airway by simultaneously stiffening and/or retracting the tongue base, lateral pharyngeal walls and soft palate. All of these effects have a beneficial effect on sleep disordered breathing.

A further advantage of the PGF is that it is easily accessible to both the physician and patient. The PGF is not normally seen during examination of the mouth as it is in a folded state and hidden by the tongue surface above it. However, the PGF can be easily palpated by sliding a finger along the floor of the mouth next to the mandible, at the level of the edge of the mandible a smooth vertical wall is reached which blocks entry into the pharynx; this is the PGF. To visualize the PGF the tongue can be retracted medially with a tongue blade.

A further advantage of the PGF is that it does not have a lot of sensory innervation. The area of the mouth around the PGF is highly sensitive. Specifically, the tonsillar pillars and the tongue surface next to the PGF are the most sensitive areas of the upper airway that cause reflex gagging. However, it has unexpectedly been found that touching the PGF itself causes little or no gagging. Moreover, even the small amount of sensation caused by touching the PGF disappears within minutes.

A further advantage of the PGF is that it is thin and easy to puncture yet contains enough connective tissue to provide a firm interface with a retractor. Anatomical studies by the inventor have shown that the PGF has few neurovascular structures and is 1-3 mm in thickness. Therefore any piercing or puncturing of the PGF is safe.

The invention consists of using an LTR to displace the PGF or neighboring tissue.

The most preferable retraction would be in an anterior direction as the retraction displaces the entire base of tongue anteriorly thereby increasing the retroglossal and retropalatal airspace. Also preferable is inferior retraction of the PGF as this displaces the tongue base inferiorly thereby removing tissue volume from the retropalatal area, the narrowest part of the upper airway. Lateral retraction would stiffen and flatten the posterior surface region of the tongue base. Less preferable is posterior or medial retraction.

This retraction could be unilateral but is preferably bilateral. This retraction could be acute, just during an obstructive episode, or semi acute, overnight while sleeping, or for extended durations. Extended durations of retraction would cause tissue remodeling that would cause the tongue to tend to remain in a more anterior position even without any force applied.

In one embodiment an LTR is inserted across the PGF and passes across the frenulum to attach to a similarly implanted LTR on the opposite side (15B).

In one embodiment the retractor lays against the PGF but the shaft passes through the tongue (15C) to an external anchor.

In one embodiment the retractor is implanted within the PGF or neighboring tongue tissue and passes anteriorly and inferiorly to an implanted anchor in the tongue, genioglossus muscle, and/or floor of mouth (15D).

In one embodiment the retractor is implanted against the superior PGF and the shaft passes inferiorly through or outside the PGF to an anchor that is implanted against the same PGF either on the same or opposite side (15E). This method retracts the superior PGF in an inferior direction.

In a further embodiment against the PGF and the shaft passes medially and superiorly to an anchor on the superior surface of the tongue (15F).

In a further embodiment the retractor is implanted at the tongue base and connects to two shafts that are placed at either PGF (16B).

In a further embodiment a shaft placed beneath the mucosa of the tongue base connects retractor members anterior to each PGF (16C).

In a further embodiment, a shaft placed beneath the mucosa of the tongue base is connected at either end to implanted magnets in or around the PGFs (16D). External modified anchors with magnets of opposite polarity are used to bond to the implanted magnets and anchor them to external structures.

In a further preferred embodiment, only the retractor member would be implanted in the PGF. The retractor would have a flange surface near its posterior aspect that would provide the interface against the PGF to cause anterior retraction. A second flange could be added anteriorly to prevent displacement of the conduit. A variety of coupling mechanisms could be used, FIG. (16E) shows a magnetic mechanism.

Magnets are implanted within each PGF and external modified anchors with magnets of opposite polarity are used to bond to the implanted magnets and anchor them to external structures. Many other coupling mechanisms are known in the art, non-limiting examples being hooks, clamps or screws. This embodiment is minimally invasive and allows the patient a very high degree of comfort during the day when the implant is unconnected and therefore unloaded. A variety of different shaft and anchor combinations can be tested without needing to replace the retractor implant.

Another aspect of this invention is a lateral dental anchor. This anchor may couple to the LTR using magnets, or mechanical mechanisms known in the art. The advantage of this device is that the PGF is very close to the mandibular teeth, and a secure but reversible loading of the implanted LTR can therefore be achieved with short devices. Moreover, the route from the PGF to the molar teeth is unlikely to cause the patient significant discomfort.

In still another embodiment of this invention anchors coupled to one of the following non-limiting list of structures inserts into retractors on or lateral to the PGF or pass through the PGF to tongue structures: the styloglossus, hyoglossus, chondroglossus, pharyngeal constrictor, levator and tensor of the palate, masetter, temporalis, pterygoid, facial, and platysma muscles; the hyoid, mandible, facial, and vertebral bones; the thyroid, cricoid, epiglottic cartilages; the stylohyoid, ptyrogomandibular ligaments and other fascial structures.

8. Soft Palate And Tonsillar Folds

Disclosed here are methods and devices for retracting the lateral pharyngeal walls and soft palate.

FIG. 17 shows the basic anatomy of the internal soft palate structures and some embodiments of this invention. The soft palate is a thin muscular structure that separates the nasopharynx and velopharynx from the oral cavity. It begins at the edge of the hard palate and extends downward toward the throat. In the midline it ends at the uvula, and on each side it divides into two folds that surround the palatine tonsils: the anterior tonsillar fold, also called the palatoglossal fold, inserts into the side of the tongue near the superior PGF; the posterior tonsillar fold, also called the palatopharyngeal fold, inserts into the lateral pharyngeal wall.

Excess length or thickness of the soft palate decrease the volume of the velopharynx and contribute to snoring and sleep apnea. In addition, laxity of the soft palate, and pharyngeal walls predisposes to airway collapse. The methods of this invention can reversibly or persistently thin, stiffen, and/or retract the soft palate and pharyngeal wall structures.

The loading of a soft palate LTR is analogous to the above described embodiment in the tongue. Specifically the soft palate LTR could rest in place unloaded, i.e. with a minimum tension (preferably 1-100 gms, most preferably 5-15 gms) that is sufficient to keep the shaft within tissue and the anchor and retractor resting immobile against mucosa. The patient would therefore have little or no sensation of the LTR's presence At night the LTR could be loaded by placement of a modified anchor, non-limiting examples being a bolster between the anchor and the mucosa, or connecting to a dental device.

The exact site and orientation of the lateral LTR has a great influence on whether the effects of the LTR are primarily to compress or displace tissue.

FIG. 17 shows some non-limiting examples of the same anchor site at the superior PGF can have multiple preferred embodiments with different beneficial effects:

LTR #1 in the figure is oriented to achieve inferior displacement of the lateral aspect of the soft palate, thereby enlarging the velopharynx.

LTR #2 passes to the midline of the soft palate. The exact location, force and number of LTRs can be varied in order to best treat the specific pathology of each patient.

LTR #3 passes across the tonsil to a retractor on the pharyngeal side of the posterior tonsillar pillar. The tonsils in sleep apnea patients often are enlarged relative to normal and this enlargement contributes to the excess soft tissue of the upper airway. Tension in the shaft would compress the tonsils and decrease their volume.

LTR #4 passes from the superior PGF to the mucosa of the tongue base. This embodiment stiffens the mucosa of the tongue base and prevents the tongue base from deforming backward.

FIG. 18 shows a variety of preferred embodiments in the tonsillar folds.

FIG. 19A shows an embodiment of a midline LTR in the soft palate with an anchor near the hard palate, a shaft passing through soft tissue and a retractor head in the uvular area (FIG. 18A). The anchor element could rest against the mucosa on either the oral or pharyngeal side. The anchor would be available to couple to a modified anchor on the oral side such as a dental appliance, or a modified anchor on the pharyngeal side. The retractor member could be inserted so it faces either forward, downward or backward.

FIGS. 19B and C shows the effect of a modified anchor in bolster form on the shape and position of the soft palate. Inserting a bolster rotates, stiffens and indents the soft palate. All of which serve to decrease the susceptibility to snoring and airway obstruction. The mount of tension added by the bolster preferably ranges from 1 to 500 gm, more preferably 5 to 250 gms and most preferably 10 to 50 gms. The bolster is designed to allow the anchor head to fit into a recess in the front surface, such that after insertion the combined anchor bolster presents a smooth and soft continuous surface thereby having no effect on speech or swallowing and causing minimal discomfort to the patient.

FIG. 19D shows another preferred embodiment of the LTR which is totally implanted.

FIG. 19E shows a further embodiment whose main effect is to compress a thickened soft palate. The anchor and retractor components are aligned on either side of the soft palate. Tension in the shaft compresses and thins the tissue between them.

FIG. 19F shows an embodiment in which restraining shafts are anchored by the LTR and pass around the edge of the soft palate to keep them in position.

9. Veterinarian Embodiments

Disclosed here are methods and devices to treat sleep apnea and related disorders in mammals.

A non-limiting example of a non-human upper airway disorder is dorsal displacement of the soft palate (DDSP) in horses. Race horses are superb animal athletes that place the greatest demands on respiration. All non-human mammals have a different configuration of their upper airways. Specifically the soft palate and larynx are much closer and they usually interlock (FIG. 20A). Specifically the soft palate is firmly held around the epiglottis of the larynx so that the airway from the nose through the pharynx and into the lungs is protected and secure. In race horses this is of special importance because of the tremendous volume of air that must smoothly flow into and out of the lungs with each breath during exercise.

In some horses this interlocking of the soft palate and epiglottis breaks down and the soft palate passes backward over the epiglottis (20B). This displacement of the soft palate immediately interferes with breathing and the animal stops running. Although the cause of DDSP is not known with certainty many trainers believe that the tongue causes the displacement by moving backward and pushing the soft palate out of position. For this reason many trainers actually tie the race horse's tongue forward prior to the race, a solution that is crude and uncomfortable for the animal.

Part of this invention are methods and devices to prevent DDSP both by preventing backward displacement of the tongue and by securely coupling the soft palate to the epiglottis. In humans the conditions surrounding sleep disordered breathing involve a relaxed tongue during sleep. In horses the situation is quite different: the tongue and other upper airway structures are much larger and maximally active. Therefore the LTR must be adapted to these harsher conditions. Moreover secure prevention of backward movement of the tongue does not allow normal swallowing. Therefore it is necessary that the LTR be loaded immediately before exercise and unloaded immediately afterward. Moreover this needs to be done by the trainer, with or without the cooperation of the horse.

In one embodiment an LTR is used to prevent movement of the tongue backwards to prevent dorsal displacement of the soft palate in a horse. The situation in the equine patient differs in many substantial ways from that of the human. The problem occurs when the animal is awake and exercising at frill capacity. It is believed that the tongue moves backward and pushes the soft palate out of its normal position where it is interlocked with the epiglottis (K). Therefore the retracting forces needed are much higher than those used in humans (preferably 1 gm to 50 Kgms, more preferably 10 gm to 10 Kgm, most preferably 100 gm to 1 Kgm). To accommodate these forces the LTR materials are preferably composed of stainless steel or materials of comparable tensile strength. In one embodiment an LTR passes from the tongue base to the superior surface of the tongue. The LTR is unloaded most of the time and only becomes laded when it is connected to the bit of the horse's bridle prior to exercise. In a further embodiment the LTR spans from the tongue base through the mandible where is can be accessed inside of the lip. A bolster is placed to load the LTR prior to exercise.

FIG. 20 D shows an embodiment of the LTR that takes advantage of certain unique circumstances present in horses. Specifically, a bridle is usually placed on the horse's head when racing to control the horse, and most bridle's have a bit, a bar which passes across the horse's mouth. This bit can be used as a modified anchor to couple and load the LTR.

Alternative embodiments secure the soft palate and epiglottis together. FIG. 20E shows an embodiment wherein LTR passes from the soft palate to the epiglottis to resist displacement, and if it occurs, to rapidly restore the interlocked configuration. FIG. 20F shows an embodiment where an LTR from each PGF attaches to the lateral aspects of each soft palate.

10. Non-Invasive Embodiments

Disclosed here are methods and devices for non-invasively retracting mucosa and displacing soft tissue volume for the treatment of sleep apnea and related disorders. A major advantage is that no surgical procedure is needed, and non-invasive devices can be easily inserted and removed by the patient.

At present the only effective non-invasive therapy for sleep apnea is CPAP. CPAP displaces the soft tissue with air pressure and, although effective in many cases, it is uncomfortable for the patient and has a very low compliance rate. The only other non-invasive therapies which have some effect on sleep apnea are the dental devices. Dental devices work by moving the jaw down and forward, thereby indirectly moving the entire floor of mouth and tongue. By this method the airway is expanded and the mucosa connecting the jaw to the pharynx is slightly stretched and stiffened. Unfortunately the joint connecting the jaw to the skull can only be stretched a small amount so that there is a limit to how much the airway can be expanded. Therefore, at present, dental devices are only effective in some mild cases.

It is not obvious how any LTR could retract the tongue and other soft tissue without puncturing, mucosa. The tongue and pharynx are highly sensitive to contact and any stimulation causes gagging. Moreover, the whole region is covered with slippery mucosa and is always moving. Therefore it is not obvious that a device can remain in place without some firm anchoring to tissue.

In one embodiment a retractor 'hooks' the PGF much like eyeglasses hook over the ear (FIGS. 21B and C). The retractor lies within the groove formed by the base of tongue and the lateral pharyngeal wall with its main contact along the vertical back surface of the PGF. In one embodiment the retractor is preferably thin, soft and form fitted to comfortably distribute force to the mucosa. A non-limiting example is a soft gel like silicone. The length of the retractor is preferably 1 mm to 100 cm, more preferably 0.5 cm to 5 cm, most preferably 1 cm to 2 cm. The retractor can extend downward as far as the esophagus and in some embodiments retract the upper esophageal sphincter, the pyriform sinuses, the vocal folds, the aryepiglottic folds, the epiglottis and/or the lateral pharyngeal walls.

Another preferable shape for the retractor is a wedge shape as shown in FIG. 21H. The wider plane of the wedge would preferably be 1-10 mm wide. This width compresses the tongue base and decreases its compliance, thereby helping to prevent its posterior collapse. The wider base can then also coax the tongue base anteriorly (FIGS. 21G and H).

In some embodiments the shaft passes directly from the top of the retractor over the PGF to connect with one or more of the anchoring sites disclosed herein. The closest structures are the teeth and particularly the molars. Dental appliances that are affixed to molars are well known in the art. These appliances can have a wide variety of mechanisms to attach to the shaft. One common method similar to that used in orthodontics is to use rubber bands. In this case a rubber band would attach to the retractor at one end and the anchor on a molar tooth at the other. The advantage of this embodiment is that the device is easily removable and replaceable, completely adjustable, and the distance traveled by the shaft to anchor could be very short, thereby achieving the goal with minimal patient discomfort.

The hook retractor can be used at many sites disclosed herein. However, to remain in place the hook requires that it be loaded while in position. The PGF site is advantageous as the retractor is surrounded by tissue on all sides and even the top is covered by the overhanging lateral part of the tongue.

In another preferred embodiment of this invention the retractor is designed to remain attached to the tissue fold indefinitely by non-invasive means. In one preferred embodiment the mechanical retractor is clipped over the tissue fold so that it can remain in place for extended periods without connection to an anchor (FIG. 22). Tissue folds are malleable such that compression at the ends of the clips indents the tissue and resists its migration out of position (22A). Compressive force at the ends of the arms of the clip would preferably be mechanical. These forces may be generated by the plastic physical properties of the clip, a spring incorporated at its lower end, an inserted length of nitinol or other material that maintains force, or by magnets within the anchor/retractor components (22B). Magnets can also be used to reversibly couple to a modified anchor. This embodiment can both compress the mucosa and retract the edge of the soft tissue fold (22C). Two clips can be connected by a shaft that is exerting force in an expanding direction (protract or lengthen) (22D).

The clip non-invasive retractors can be used in all sites within the upper airway where mucosal folds are present or where they can be formed by grasping tissue. These include without limitation, the PGF, frenulum, lateral tongue surface, tonsillar folds (22E, F), soft palate (22G), pharyngeal walls, floor of the mouth, and aryepiglottic fold. Some of these sites have extensive sensory innervation, however, so long as the contact between the clip and mucosa is stable and immobile the sensation disappears within minutes. This loss of sensation is called habituation and is well known to sensory physiologists. The stability of the retractor to mucosa contact is increased by the use of adhesives known in the art. Adhesives effective on mucosa include but are not limited to fibrin, hydrogels, and/or cyanoacrylic glues. It is also important that the site for the clip as well as the shaft and anchor be placed such that the least amount of dynamic contact occurs between components and mucosa. In addition, for persistent use the compression between the arms of the clip should not exceed the pressure at which capillary blood circulation stops, called the perfusion pressure, which is about 25 mm Hg or 34 cm $H_2O$.

Another non-invasive embodiment of this invention are methods and devices that use a vacuum to retract or displace soft tissue. Vacuum devices are used in two different methods: a vacuum can serve to suck a retractor head onto a mucosal surface thereby attaching the retractor; the vacuum can be applied over a larger segment of the tongue and cause displacement of tongue tissue into the suction. As the volume of the tongue is constant the displacement of tissue must come from other parts of the tongue, most preferably the tongue base.

In one method a vacuum is used to couple a retractor to mucosa. Then the retractor can be attached to modified anchors as described herein. A second method of using a vacuum is to displace soft tissue volume. This is preferably used on the tongue by a relatively larger device that sucks tissue volume into the vacuum device and thereby changes the shape of the tongue such that volume is removed from the tongue base.

The vacuum retractor could be a suction cup type well known in the art and the vacuum formed by pressing against the mucosa. Preferably the interface between device and mucosa has well defined edges with interior walls at 90° or greater. This embodiment suctions small amount s of tissue into the opening and their presence provides resistance to shear forces acting at the suction site (23J). The vacuum retractor could also be connected to a vacuum source via a tube leading from the vacuum retractor out of the mouth. In another embodiment a small air pump could be located in the mouth. This pump may be passive, composed of a small bladder with a one way valve such that movements of the tongue or jaw that compress the bladder force air out of it through the one way valve. The elastic drive of the bladder to return to its larger volume shape forms the vacuum.

After the vacuum retractor couples to the mucosa it can be displaced forward by a shaft similar to those used for the other embodiments. The vacuum retractor could be a single suction interface or multiple smaller interfaces; mini suction cups. Viscous mucoid material or adhesive could be applied to the mucosa to aid in maintaining a seal. The vacuum retractor is most preferably applied to the anterior surface of the PFG. Other preferred sites are the lateral and inferior tongue surface. Those skilled in the art can understand that the vacuum could be applied at all locations that retraction is beneficial.

Another embodiment of this invention is to increase the pharyngeal airspace by depressing the floor of the mouth. The floor of the mouth (FOM) is composed of muscles and other soft tissue that attaches to the hyoid posteriorly and the mandible anteriorly and laterally. The tongue sits on the FOM and follows its movements. For example when the jaw is moved forward or downward the tongue moves along with it. Similarly when the hyoid bone moves forward it displaces the back of the tongue in the same direction. Some surgical procedures try to take advantage of this relationship by wiring the hyoid bone in a more forward position by wiring it to the front of the mandible. Unfortunately the hyoid bone has many other attachments that resist being repositioned.

This invention does not focus on moving the boney attachments of the FOM but instead on moving the soft tissue of the FOM itself. Specifically, the bottom of the tongue (root of the tongue) that rests on the FOM is triangular shaped and smaller then the overall area of the FOM (FIG. 23). Therefore the FOM can be reached between the tongue root and the mandible. When this area is depressed the root of the tongue is depressed as well. Although the entire exposed FOM can be depressed, this is inefficient, as the most important area to move is the tongue base.

In the preferred embodiment the area of the FOM around the tongue base is depressed thereby moving the tongue base down and increasing the pharyngeal airspace. For practical purposes the PGF places a limit on how far back the FOM can be reached. In one embodiment an LTR with a silicon bolster of 0.5 cm×0.5 cm×1 cm is situated longitudinally alongside the undersurface of the tongue with one end abutting the PGF. Downward pressure is achieved by a dental appliance attached to the molar teeth. Not all of the downward movement of the local area of FOM depression is transferred to the tongue. However, any significant increase in the pharyngeal airspace is beneficial.

In addition to depression of the FOM, displacement force can be exerted forward (anterior), inward (medial) or outward (lateral). Forward displacement is beneficial because the pharyngeal airspace is expanded to the extent that the tongue base also moves forward. Inward movement is beneficial if both sides exert a grasping force on the tongue and thereby resist its backward collapse. Outward movement is also beneficial to the extent that it stretches and tenses tongue tissue thereby also preventing backward collapse.

It is to be understood that the exemplary embodiments are merely illustrative of the invention and that many variations of the above-described embodiments can be devised by one skilled in the art without departing from the scope of the invention. It is therefore intended that all such variations be included within the scope of the following claims and their equivalents.

What is claimed is:

1. A method for treatment of a breathing disorder, the method comprising:
   inserting a flexible shaft through a soft tissue of a patient's tongue;
   connecting a retractor member at or near a first end of the flexible shaft;
   connecting an anchor member at or near a second end of the flexible shaft;

positioning at least one of the retractor member or the anchor member on an external surface of the soft tissue; and adjusting the anchor member to impart a compressive force on the soft tissue through the flexible shaft toward the retractor member that prevents deformation of at least a portion of the soft tissue, wherein the compressive force on the soft tissue retracts a surface of the soft tissue toward the anchor member and displaces a portion of the soft tissue, including at least a portion of a base of the patient's tongue, toward the retractor member to prevent obstruction of the patient's airway, wherein the retractor member and the anchor member have sufficient area to impart the compressive force on the soft tissue.

2. The method according to claim 1, further comprising removably attaching an adjustment member to the,
wherein the attachment of the adjustment member changes the tension between the retractor member and the anchor member.

3. The tissue retractor assembly method of claim 2 wherein the adjustment member is a bolster disposed between the retractor member and the anchor member and is disposed between an external surface of the soft tissue and the anchor member.

4. The method of claim 3 wherein the bolster is substantially v-shaped with a concave surface adapted to complement the external surface of the soft tissue.

5. The method of claim 3 wherein the bolster has a cleft, and at least a portion of the flexible shaft is sized to fit within the cleft.

6. The method of claim 2 wherein the adjustment member reversibly modifies the flexible shaft.

7. The method of claim 6 wherein the adjustment member reversibly changes the length of the flexible shaft.

8. The method of claim 2 wherein the adjustment member is sized and shaped to distribute force.

9. The method of claim 2 wherein the adjustment member reversibly changes the surface area of the anchor member.

10. The method of claim 1 further comprising the step of:
attaching the anchor member to a dental bolster.

11. The method of claim 1 further comprising the step of:
attaching the anchor member to a modified anchor,
wherein the modified anchor is fixed to a tissue located in the patient's oral cavity or pharynx.

12. The method of claim 1 wherein the flexible shaft is elastic.

* * * * *

UNITED STATES PATENT AND TRADEMARK OFFICE
CERTIFICATE OF CORRECTION

PATENT NO. : 10,524,954 B2
APPLICATION NO. : 11/672019
DATED : January 7, 2020
INVENTOR(S) : Ira Sanders Page 1 of 1

It is certified that error appears in the above-identified patent and that said Letters Patent is hereby corrected as shown below:

In the Claims

Column 33, Line 20, Claim 3, after "The" delete "tissue retractor assembly"

Signed and Sealed this
Second Day of June, 2020

Andrei Iancu
*Director of the United States Patent and Trademark Office*